(12) United States Patent
Kang et al.

(10) Patent No.: US 6,949,652 B2
(45) Date of Patent: Sep. 27, 2005

(54) CRYSTALLINE FORMS OF 3-ISOPROPYL-6-[4-(2,5-DIFLUORO-PHENYL)-OXAZOL-5-YL]-[1,2,4]TRIAZOLO-[4,3-A]PYRIDINE

(75) Inventors: Ming Kang, Salem, CT (US); Zheng Jane Li, Quaker Hill, CT (US); Zhengong Bryan Li, East Lyme, CT (US); Yong Tao, Salem, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/649,194

(22) Filed: Aug. 27, 2003

(65) Prior Publication Data

US 2004/0143119 A1 Jul. 22, 2004

Related U.S. Application Data

(60) Provisional application No. 60/407,158, filed on Aug. 30, 2002.

(51) Int. Cl.[7] .............. C07D 471/04; A61K 31/437
(52) U.S. Cl. .............. 546/119; 546/118; 514/303
(58) Field of Search ................. 546/119, 118; 514/303

(56) References Cited

U.S. PATENT DOCUMENTS

| | | | |
|---|---|---|---|
| 5,716,955 A | 2/1998 | Adams et al. | 514/235.8 |
| 5,716,972 A | 2/1998 | Adams et al. | 514/341 |
| 5,717,100 A | 2/1998 | Selnick et al. | 546/194 |
| 5,756,499 A | 5/1998 | Adams et al. | 514/235.8 |
| 5,777,097 A | 7/1998 | Lee et al. | 536/24.31 |
| 6,288,062 B1 | 9/2001 | Adams et al. | 514/236.8 |
| 6,696,464 B2 * | 2/2004 | McClure et al. | 514/303 |
| 2004/0092547 A1 * | 5/2004 | Dombroski et al. | 514/303 |

FOREIGN PATENT DOCUMENTS

| | | | |
|---|---|---|---|
| EP | 1247810 | 10/2002 | ......... C07D/403/04 |
| WO | 9901449 | 1/1999 | ......... C07D/401/04 |
| WO | 9961440 | 12/1999 | ......... C07D/403/14 |
| WO | 0006563 | 2/2000 | ......... C07D/401/04 |
| WO | 0031065 | 6/2000 | ......... C07D/401/04 |
| WO | 0035911 | 6/2000 | ......... C07D/405/14 |
| WO | 0040243 | 7/2000 | ......... A61K/31/444 |
| WO | 0041698 | 7/2000 | ......... A61K/31/535 |
| WO | 0063204 | 10/2000 | ......... C07D/413/00 |
| WO | 0272576 | 9/2002 | ......... C07D/403/14 |
| WO | 0272579 | 9/2002 | ......... C07D/471/04 |

OTHER PUBLICATIONS

The Journal of Biological Chemistry, vol. 271, No. 40, pp. 24313–24316 (1996).
Bioorganic & Medicinal Chemistry Letters, 10, pp. 2047–2050 (2000); and.
Bioorganic & Medicinal Chemistry Letters, 11, pp. 9–12 (2001).

* cited by examiner

*Primary Examiner*—Evelyn Mei Huang
(74) *Attorney, Agent, or Firm*—Julie M. Lappin; Garth Butterfield

(57) ABSTRACT

The present invention relates to novel crystalline forms of 3-isopropyl-6-[4-(2,5-difluoro-phenyl)-oxazol-5-yl]-[1,2,4]triazolo-[4,3-a]pyridine to pharmaceutical compositions containing such crystal forms and to methods of treatment. 3-Isopropyl-6-[4-(2,5-difluoro-phenyl)-oxazol-5-yl]-[1,2,4]triazolo-[4,3-a]pyridine is a potent inhibitor of MAP kinases, preferably p38 kinase (MAPK14/CSBP/RK kinase). 3-Isopropyl-6-[4-(2,5-difluoro-phenyl)-oxazol-5-yl]-[1,2,4]triazolo-[4,3-a]pyridine is useful in the treatment of inflammation, osteoarthritis, rheumatoid arthritis, cancer, reperfusion or ischemia in stroke or heart attack, autoimmune diseases and other disorders.

17 Claims, 16 Drawing Sheets

PXRD of Form A

Experimental A

Simulated A

PXRD pattern of Form B

Experimental B

Simulated B

PXRD of Form C

PXRD of Form D

PXRD of Form E

13C CPMAS NMR spectrum of form B
20 kHz spinning, 28407 scans with 2.5 mm probe (~12 mg)

DSC of Form A

The thermal profile of form A by DSC shows multiple events, at peak temperatures about 110, 123, 148-152 and 174°C. Depending on the sample history, events at 123 and 148-152 may or may not be present.

DSC of Form B

The thermal profile of form B displays one melting endotherm event at onset temperature about 173 to 175°C.

DSC of Form C

Form C has three thermal events at peak temperature about 153, 154 and 174°C shown in DSC thermogram.

Form D DSC1

Form D DSC2

By DSC, form D shows a broad endotherm between 30 to 130°C and a sharp melting endotherm with on set temperature about 174°C. The peak temperature of the first endotherm peak may vary from 80 to 115°C depending on drying condition.

Form E

By DSC, form E shows a broad endotherm with a peak temperature about 116°C and a sharp melting endotherm with on set temperature about 174°C.

CRYSTALLINE FORMS OF 3-ISOPROPYL-6-[4-(2,5-DIFLUORO-PHENYL)-OXAZOL-5-YL]-[1,2,4]TRIAZOLO-[4,3-A]PYRIDINE

This application claims the benefit of provisional application No. 60/407158, filed on Aug. 30, 2002

The present invention relates to novel crystalline forms of 3-isopropyl-6-[4-(2,5-difluoro-phenyl)-oxazol-5-yl]-[1,2,4]triazolo-[4,3-a]pyridine to pharmaceutical compositions containing such crystal forms and to methods of treatment. 3-isopropyl-6-[4-(2,5-difluoro-phenyl)-oxazol-5-yl]-[1,2,4]triazolo-[4,3-a]pyridine is a potent inhibitor of MAP kinases, preferably p38 kinase (MAPK14/CSBP/RK kinase). 3-Isopropyl-6-[4-(2,5-difluoro-phenyl)-oxazol-5-yl]-[1,2,4]triazolo-[4,3-a]pyridine is useful in the treatment of inflammation, osteoarthritis, rheumatoid arthritis, cancer, reperfusion or ischemia in stroke or heart attack, autoimmune diseases and other disorders.

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phospholipases are the essential machinery by which the signal is further transmitted within the cell [Marshall, J. C., Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/threonine(s) residues [Hunter, T., Methods in Enzymology (Protein Kinase Classification), p. 3, Hunter, T.; Sefton, B. M.; eds. vol. 200, Academic Press; San Diego, 1991].

For most biological responses, multiple intracellular kinases are involved and an individual kinase can be involved in more than one signaling pathway. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J., Cell, 80, 179 (1995); Herskowitz, I., Cell, 80, 187 (1995); Hunter, T., Cell, 80, 225 (1995); Seger, R., and Krebs, E. G., FASEB J., 726–735 (1995)].

While many signaling pathways are part of normal cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). Early evidence suggesting that the signal transduction pathway leading to LPS-induced cytokine biosynthesis involved protein kinases came from studies of Weinstein [Weinstein, et al., J. Immunol, 151, 3829(1993)] but the specific protein kinases involved were not identified. Working from a similar perspective, Han [Han, et al., Science 265, 808(1994)] identified murine p38 as a kinase which is tyrosine phosphorylated in response to LPS. Additional evidence of the involvement of the p38 kinase in LPS-stimulated signal transduction pathway leading to the initiation of proinflammatory cytokine biosynthesis was provided by the discovery of p38 kinase (MAPK14, CSBP 1 and 2) by Lee [Lee; et al., Nature, 372, 739(1994)] as the molecular target for a novel class of anti-inflammatory agents. Thus, compounds which inhibit p38 will inhibit IL-1 and TNF synthesis in human monocytes. Such results have been reported by [Lee, et al., Int. J. Immunopharmac., 10(7), 835(1988)] and [Lee et al., Annals N.Y. Acad. Sci., 696, 149(1993)].

It is now accepted that CSBP/p38 is one of several kinases involved in a stress-response signal transduction pathway which is parallel to and largely independent of the analogous mitogen-activated protein kinase (MAP) kinase cascade. Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27. It is now known that MAPKAP-2 is essential for LPS induced TNFα biosynthesis [Kotlyarov, et al., Nature Cell Biol., 1, 94 (1999), see also Cohen, P., Trends Cell Biol., 353–361(1997)].

In addition to inhibiting IL-1 and TNF, CSBP/p38 kinase inhibitors also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1 stimulated synthesis of collagenase and stromelysin. These and additional data demonstrate that CSBP/p38 is involved not only cytokine synthesis, but also in cytokine signaling [CSBP/p38 kinase reviewed in Cohen, P., Trends Cell Biol., 353–361 (1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g.,. Dinarello, et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, cachexia, psoriatic arthritis, Reiter's syndrome, rheumatoid arthritis, gout, traumatic arthritis, rubella arthritis, and acute synovitis. Other studies also link IL-1 activity to diabetes and pancreatic β cells, Dinarello, J. Clinical Immunology, 5 (5), 287–297 (1985).

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid information, scar tissue formation, Crohn's disease, ulcerative colitis, or pyrosis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well lysosomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increase in IL-8 production (which is responsible for chemotaxis of neutrophils into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.,* 279 (3); 1453–1461. (1996); Griswold, et al., *Pharmacol. Comm.,* 7, 323–229 (1996)].

There remains a need for treatment, in this field, for compounds which are cytokine suppressive anti-inflammatory drugs, i.e., compounds which are capable of inhibiting the MAPK14/CSBP/p38/RK kinase.

Other kinases differentially affected by the compounds of the present invention include: Extracellular signal regulated kinase-1 (ERK1 or MAPK3), Extracellular signal regulated kinase-2 (ERK2 or MAPK2), Extracellular signal regulated kinase-3 (ERK3 or MAPK6), Extracellular signal regulated kinase-5 (ERK5 or MAPK7), Extracellular signal regulated kinase-6 (ERK6 or MAPK12), MAPK1, MAPK4, MAPK8, MAPK9, MAPK10, MAPK11, and MAPK13.

MAPK14/CSBP/p38/RK kinase inhibitors are well known to those skilled in the art. U.S. Provisional Applications 60/274,791, 60/274,840 and 60/281,331, filed Mar. 9, 2001, Mar. 9, 2001 and Apr. 4, 2001, respectively, and entitled "Novel Antiinflammatory Compounds," "Novel Triazolopyridine Antiinflammatory Compounds" and "Novel Benzotriazole Antiinflammatory Compounds," respectively, refer to certain inhibitors of MAP kinases, preferably p38 kinase. International Patent Publication WO 00/40243, published Jul. 13, 2000, refers to pyridine substituted pyridine compounds and states that these compounds are p38 inhibitors. International Patent Publication WO 00/63204, published Oct. 26, 2000, refers to substituted azole compounds and states that these compounds are p38 inhibitors. International Patent Publication WO 00/31065, published Jun. 2, 2000, refers to certain heterocyclic compounds and states that these compounds are p38 inhibitors. International Patent Publication WO 00/06563, published Feb. 10, 2000, refers to substituted imidazole compounds and states that these compounds are p38 inhibitors. International Patent Publication WO 00/41698, published Jul. 20, 2000, refers to certain ω-carboxy aryl substituted diphenyl urea compounds and states that these compounds are p38 inhibitors. U.S. Pat. No. 6,288,062 refers to certain substituted oxazole compounds and states that these compounds are p38 inhibitors. U.S. Pat. No. 5,716,955 refers to certain substituted imidazole compounds and states that these compounds are p38 inhibitors. U.S. Pat. No. 5,716,972 refers to certain pyridinyl substituted imidazole compounds and states that these compounds are p38 inhibitors. U.S. Pat. No. 5,756,499 refers to certain substituted imidazole compounds and states that these compounds are p38 inhibitors.

SUMMARY OF THE INVENTION

The present invention relates to crystal forms of 3-isopropyl-6-[4-(2,5-difluoro-phenyl)-oxazol-5-yl]-[1,2,4]triazolo[4,3-a]pyridine.

Polymorphs are different crystal forms of the same compound. Different crystal forms have different physical properties such as different melting point, single crystal x-ray, powder x-ray, and solid state NMR. The present invention relates to five different crystal forms of 3-isopropyl-6-[4-(2,5-difluoro-phenyl)-oxazol-5-yl]-[1,2,4]triazolo[4,3-a]pyridine, designated Forms A–E.

More specifically, the compound 3-isopropyl-6-[4-(2,5-difluoro-phenyl)-oxazol-5-yl]-[1,2,4]triazolo[4,3-a]pyridine exists as a crystal Form A having the single crystal x-ray crystallographic data

| | Form A |
|---|---|
| Empirical formula | $C_{18}H_{14}N_4OF_2$ |
| Formula weight | 340.33 |
| Temperature (K) | 268 (2) |
| Crystal size (mm) | 0.04 × 0.06 × 0.15 |
| Space group | $P2_1/n$ monoclinic |
| Unit cell dimensions | a = 6.6546 (11) Å |
| | b = 25.675 (4) Å |
| | c = 10.5455 (17) Å |
| | α = 90° |
| | β = 98.918 (5)° |
| | γ = 90° |
| Z (per formula) | 4 |
| Density (g/cm$^3$) | 1.270 |
| R | 0.0783 |

More specifically, the crystalline A form of the compound 3-isopropyl-6-[4-(2,5-difluoro-phenyl)-oxazol-5-yl]-[1,2,4]triazolo[4,3-a]pyridine has powder x-ray defraction peaks at angle 2-theta of 9.1, 13.8, 17.4 and 22.6. The crystalline A form of the compound 3-isopropyl-6-[4-(2,5-difluoro-phenyl)-oxazol-5-yl]-[1,2,4]triazolo[4,3-a]pyridine also has a Differential Scanning Calorimetry melting endotherm at 148–152° C.

The compound 3-isopropyl-6-[4-(2,5-difluoro-phenyl)-oxazol-5-yl]-[1,2,4]triazolo[4,3-a]pyridine also exists as a crystal Form B having the single crystal x-ray crystallographic data

| Form B | |
|---|---|
| Empirical formula | $C_{18}H_{14}N_4OF_2$ |
| Formula weight | 340.33 |
| Temperature (K) | 298 (2) |
| Crystal size (mm) | 0.10 × 0.20 × 0.24 |
| Space group | $P2_1/c$ monoclinic |
| Unit cell dimensions | a = 20.7164 (6) Å |
| | b = 10.7621 (3) Å |
| | c = 14.3522 (4) Å |
| | α = 90° |
| | β = 92.1490 (10)° |
| | γ = 90° |
| Z (per formula) | 8 |
| Density (g/cm³) | 1.414 |
| R | 0.0450 |

More specifically, the crystalline B form of the compound 3-isopropyl-6-[4-(2,5-difluoro-phenyl)-oxazol-5-yl]-[1,2,4]triazolo[4,3-a]pyridine has powder x-ray detraction peaks at angle 2-theta of 8.5, 11.2, 14.8, 16.9, 19.7, 22.3, 26.0 and 27.9. More specifically, the crystalline B form of the compound 3-isopropyl-6-[4-(2,5-difluoro-phenyl)-oxazol-5-yl]-[1,2,4]triazolo[4,3-a]pyridine, has a $^{13}C$ ss-NMR chemical shifts of 159.2, 157.2, 156.0, 154.9, 153.0, 150.2, 144.4, 142.4, 129.2, 125.3, 123.7, 121.9, 112.0, 118.3, 116.4, 114.9, 24.8, 20.8, 18.7, and 17.0. More specifically, the crystalline B form of the compound 3-isopropyl-6-[4-(2,5-difluoro-phenyl)-oxazol-5-yl]-[1,2,4]triazolo[4,3-a]pyridine, has a Differential Scanning Calorimetry melting endotherm at 173–175° C.

The compound 3-isopropyl-6-[4-(2,5-difluoro-phenyl)-oxazol-5-yl]-[1,2,4]triazolo[4,3-a]pyridine also exists as a crystal Form C having powder x-ray defraction peaks at angle 2-theta of 7.4, 12.8, 14.8, 19.6, 22.3, 25.7 and 26.8 and Differential Scanning Calorimetry melting endotherms at 153 and 174° C.

The compound 3-isopropyl-6-[4-(2,5-difluoro-phenyl)-oxazol-5-yl]-[1,2,4]triazolo[4,3-a]pyridine also exists as a crystal Form D having the single crystal x-ray crystallographic data

| Form D | |
|---|---|
| Empirical formula | $C_{18}H_{14}N_4OF_2 \cdot 3H_2O$ |
| Formula weight | 394.38 |
| Temperature (K) | 298 (2) |
| Crystal size (mm) | 0.40 × 0.28 × 0.10 |
| Space group | $P2_1/n$ monoclinic |
| Unit cell dimensions | a = 15.1326 (17) Å |
| | b = 6.9630 (8) Å |
| | c = 19.229 (2) Å |
| | α = 90° |
| | β = 108.087 (2)° |
| | γ = 90° |
| Z (per formula) | 4 |
| Density (g/cm³) | 1.360 |
| R | 0.0471 |

More specifically, the crystalline D form of the compound 3-isopropyl-6-[4-(2,5-difluoro-phenyl)-oxazol-5-yl]-[1,2,4]triazolo[4,3-a]pyridine has powder x-ray defraction peaks at angle 2-theta of 6.6, 16.0, 17.3, 17.6, 22.5, 25.6 and 26.4 and a Differential Scanning Calorimetry melting endotherm at 177° C.

The compound 3-isopropyl-6-[4-(2,5-difluoro-phenyl)-oxazol-5-yl]-[1,2,4]triazolo[4,3-a]pyridine also exists as a crystal Form E having Differential Scanning Calorimetry melting endotherms at 116 and 177° C. More specifically, the crystalline E form of the compound 3-isopropyl-6-[4-(2,5-difluoro-phenyl)-oxazol-5-yl]-[1,2,4]triazolo[4,3-a]pyridine has powder x-ray defraction peaks at angle 2-theta of 7.7, 8.4, 15.5, 17.2, 23.0, 26.7 and 28.6.

The present invention also relates to the acceptable acid addition salts of 3-isopropyl-6-[4-(2,5-difluoro-phenyl)-oxazol-5-yl]-[1,2,4]triazolo-[4,3-a]pyridine. The acids which are used to prepare the acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds and prodrugs of the present invention can exist in several tautomeric forms, including the enol and imine form, the keto and enamine form and geometric isomers and mixtures thereof. All such tautomeric forms are included within the scope of the present invention. Tautomers exist as mixtures of tautomers in solution. In solid form, usually one tautomer predominates. Even though one tautomer may be described, the present invention includes all tautomers of the present compounds.

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, $(C_1–C_6)$alkoxy, $(C_6–C_{10})$aryloxy, trifluoromethoxy, difluoromethoxy or $(C_1–C_6)$alkyl. The phrase "each of said alkyl" as used herein refers to any of the preceding alkyl moieties within a group such alkoxy, alkenyl or alkylamino. Preferred alkyls include $(C_1–C_4)$alkyl, most preferably methyl.

As used herein, the term "halogen" includes fluoro, chloro, bromo or iodo or fluoride, chloride, bromide or iodide.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "aryl" means aromatic radicals such as phenyl, naphthyl, tetrahydronaphthyl, indanyl and the like; optionally substituted by 1 to 3 suitable substituents as defined above such as fluoro, chloro, trifluoromethyl, $(C_1–C_6)$alkoxy, $(C_6–C_{10})$aryloxy, trifluoromethoxy, difluoromethoxy or $(C_1–C_6)$alkyl.

The present invention also includes isotopically-labelled 3-Isopropyl-6-[4-(2,5-difluoro-phenyl)-oxazol-5-yl]-[1,2,4]triazolo-[4,3-a]pyridine, wherein one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled 3-Isopropyl-6-[4-(2,5-difluoro-phenyl)-oxazol-5-yl]-[1,2,4]triazolo-[4,3-a]pyridine and prodrugs thereof can generally be prepared by carrying out the procedures disclosed in the Examples and Preparations below, by substituting a readily available isotopically labelled reagent for a non-isotopically labelled reagent.

3-Isopropyl-6-[4-(2,5-difluoro-phenyl-oxazol-5-yl]-[1,2,4]triazolo-[4,3-a]pyridine is capable of inhibiting proinflammatory cytokines, such as IL-1, IL-6, IL-8, and TNF and is therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these proinflammatory cytokines is of benefit in controlling, reducing and alleviating many of these disease states.

DETAILED DESCRIPTION OF THE INVENTION

Figure 1:
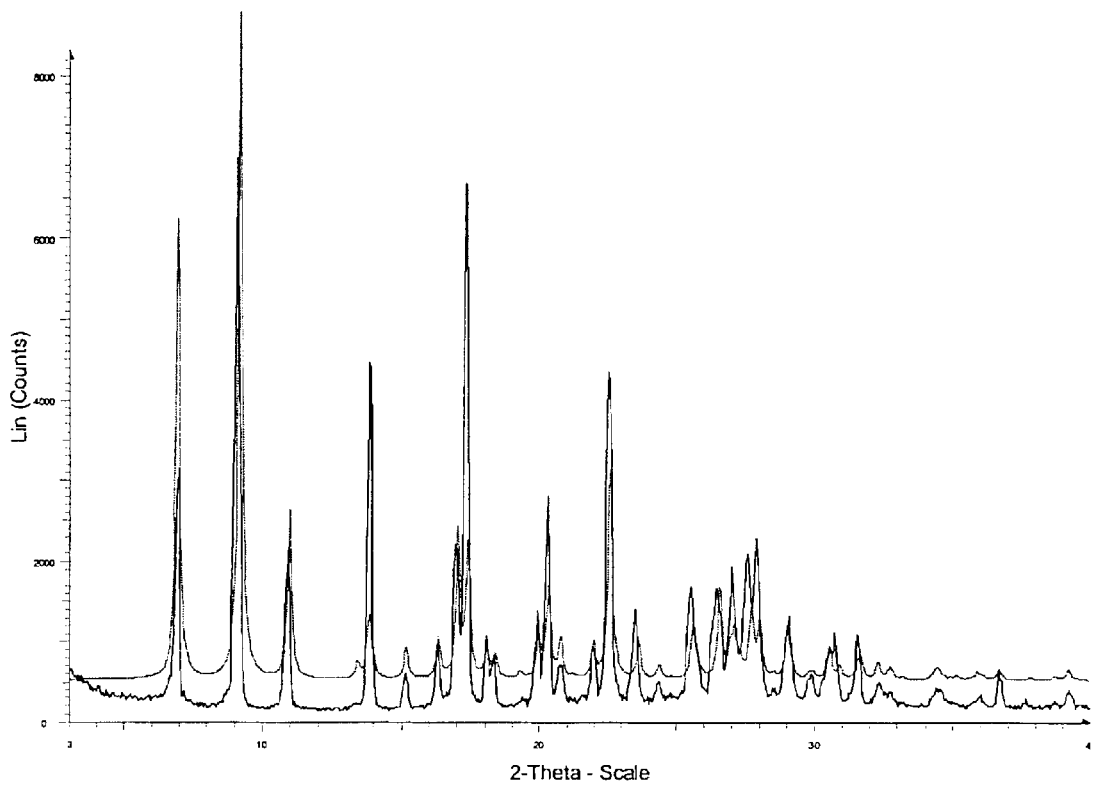
FIG. 1 is the observed X-ray diffraction pattern of 3-isopropyl-6-[4-(2,5-difluoro-phenyl)-oxazol-5-yl]-[1,2,4]triazolo[4,3-a]pyridine (Form A) (upper trace) superimposed on the calculated powder X-ray diffraction pattern for Form A (y axis is linear counts per second; X in degrees 2 theta).
Figure 2:
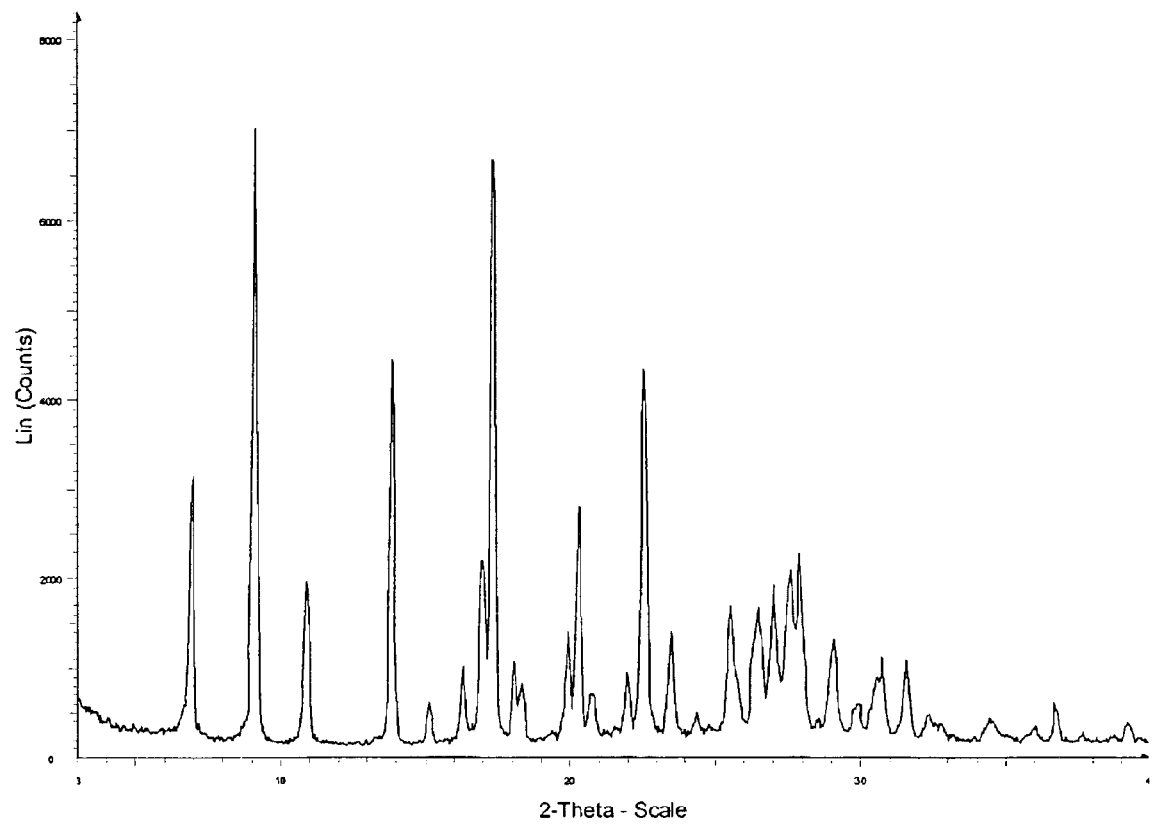
FIG. 2 is the observed powder X-ray diffraction pattern of 3-isopropyl-6-[4-(2,5-difluoro-phenyl)-oxazol-5-yl]-[1,2,4]triazolo[4,3-a]pyridine (Form A) (y axis is linear counts per second; X in degrees 2 theta).
Figure 3:
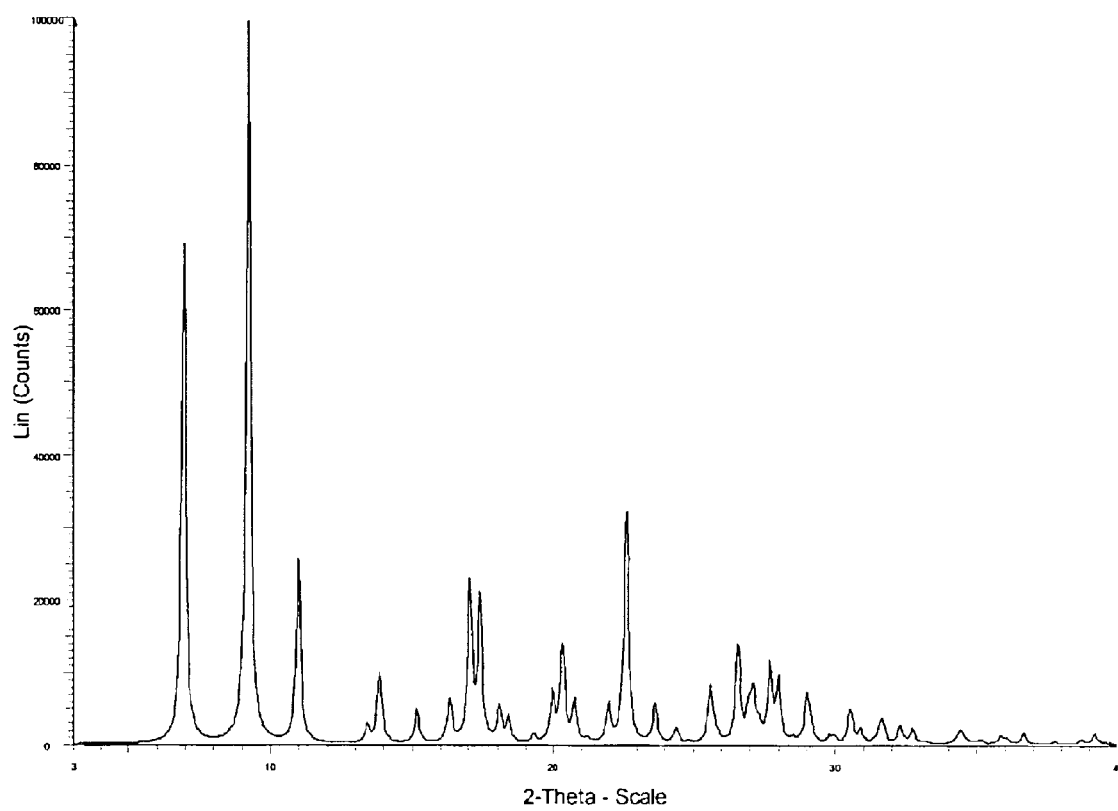
FIG. 3 is the calculated powder X-ray diffraction pattern of 3-isopropyl-6-[4-(2,5-difluoro-phenyl)-oxazol-5-yl]-[1,2,4)]triazolo[4,3-a]pyridine (Form A) (y axis is linear counts per second; X in degrees 2 theta).
Figure 4:
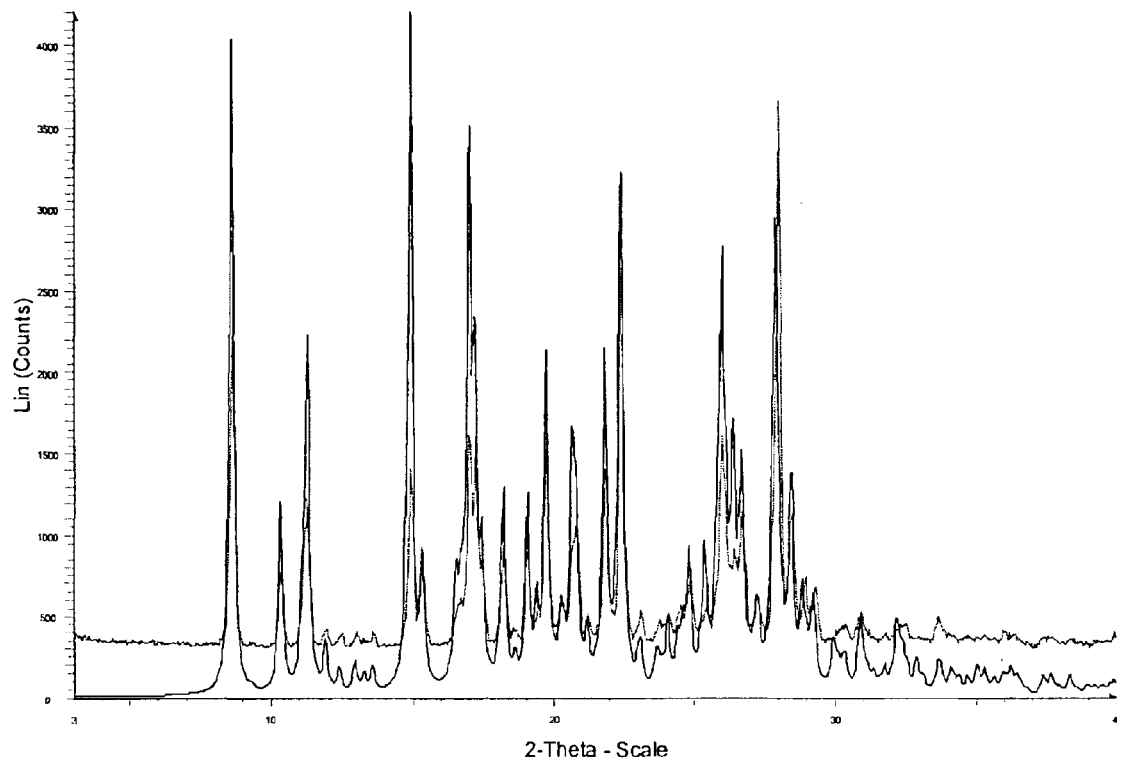
FIG. 4 is the observed X-ray diffraction pattern of 3-isopropyl-6-[4-(2,5-difluoro-phenyl)-oxazol-5-yl]-[1,2,4]triazolo[4,3-a]pyridine (Form B) (upper trace) superimposed on the calculated powder X-ray diffraction pattern for Form B (y axis is linear counts per second; X in degrees 2 theta).
Figure 5:
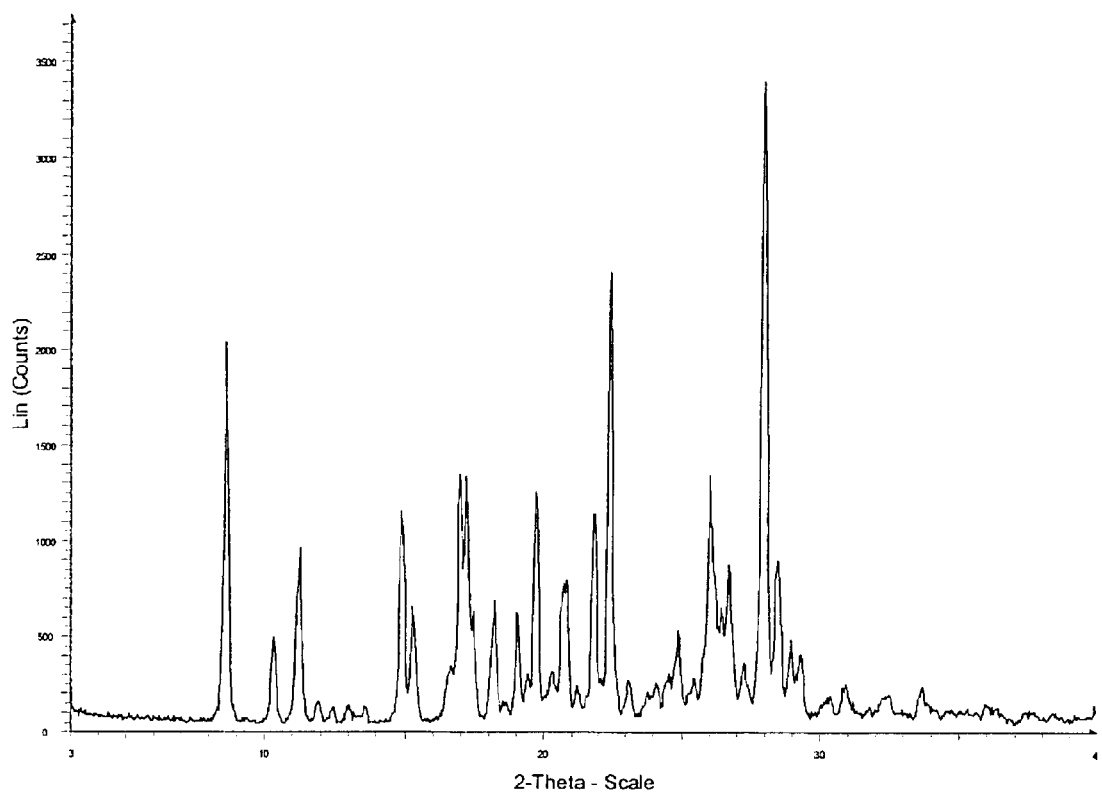
FIG. 5 is the observed powder X-ray diffraction pattern of 3-isopropyl-6-[4-(2,5-difluoro-phenyl)-oxazol-5-yl]-[1,2,4]triazolo[4,3-a]pyridine (Form B) (y axis is linear counts per second; X in degrees 2 theta).
Figure 6:
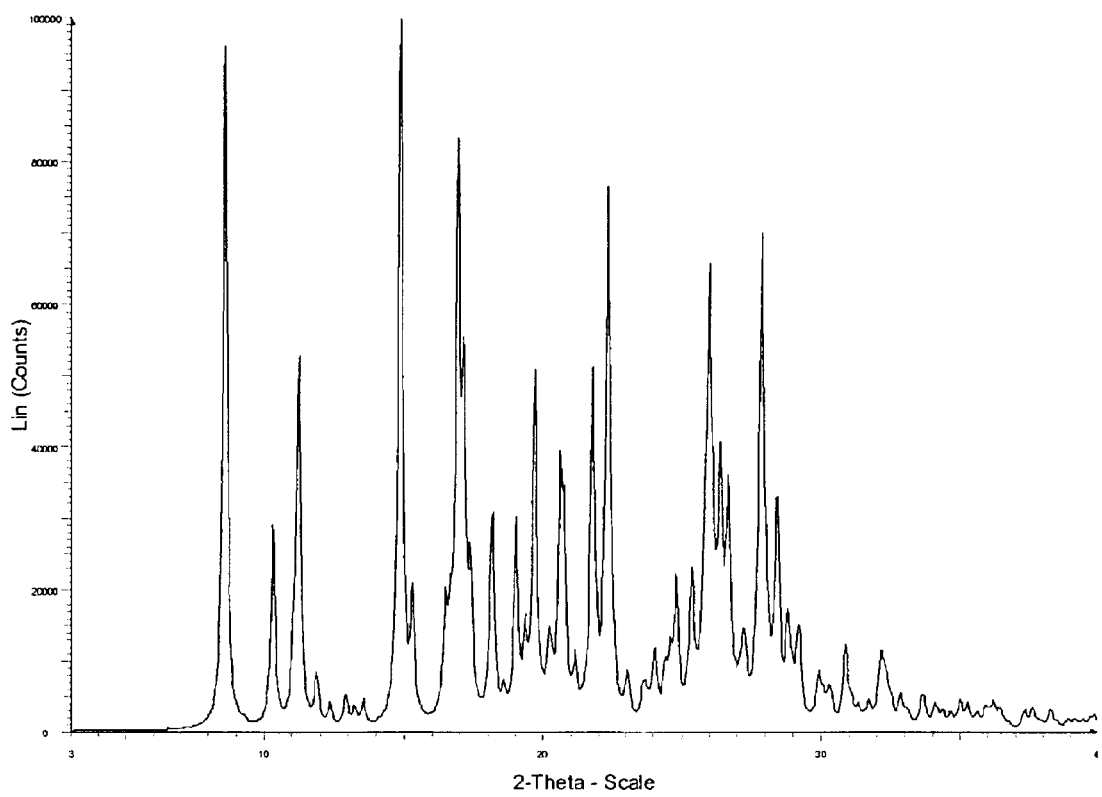
FIG. 6 is the calculated powder X-ray diffraction pattern of 3-isopropyl-6-[4-(2,5-difluoro-phenyl)-oxazol-5-yl]-[1,2,4]triazolo[4,3-a]pyridine (Form B) (y axis is linear counts per second; X in degrees 2 theta).
Figure 7:
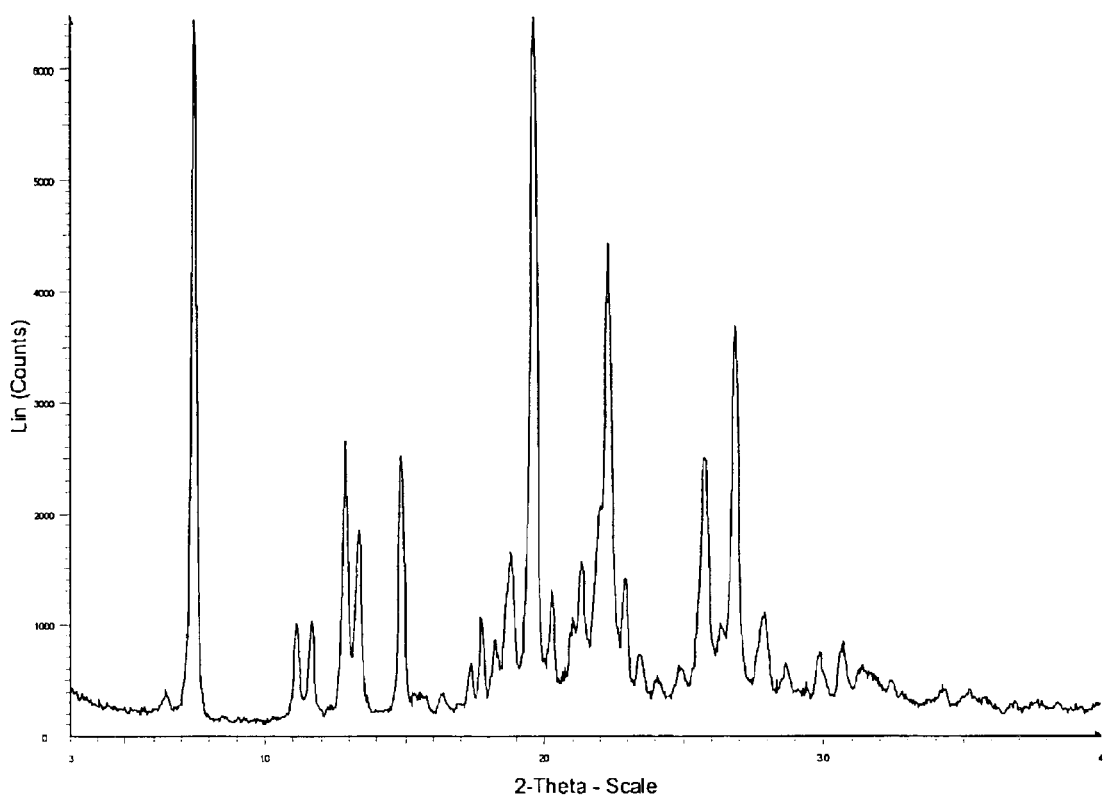
FIG. 7 is the observed powder X-ray diffraction pattern of 3-isopropyl-6-[4-(2,5-difluoro-phenyl)-oxazol-5-yl]-[1,2,4]triazolo[4,3-a]pyridine (Form C) (y axis is linear counts per second; X in degrees 2 theta).
Figure 8:
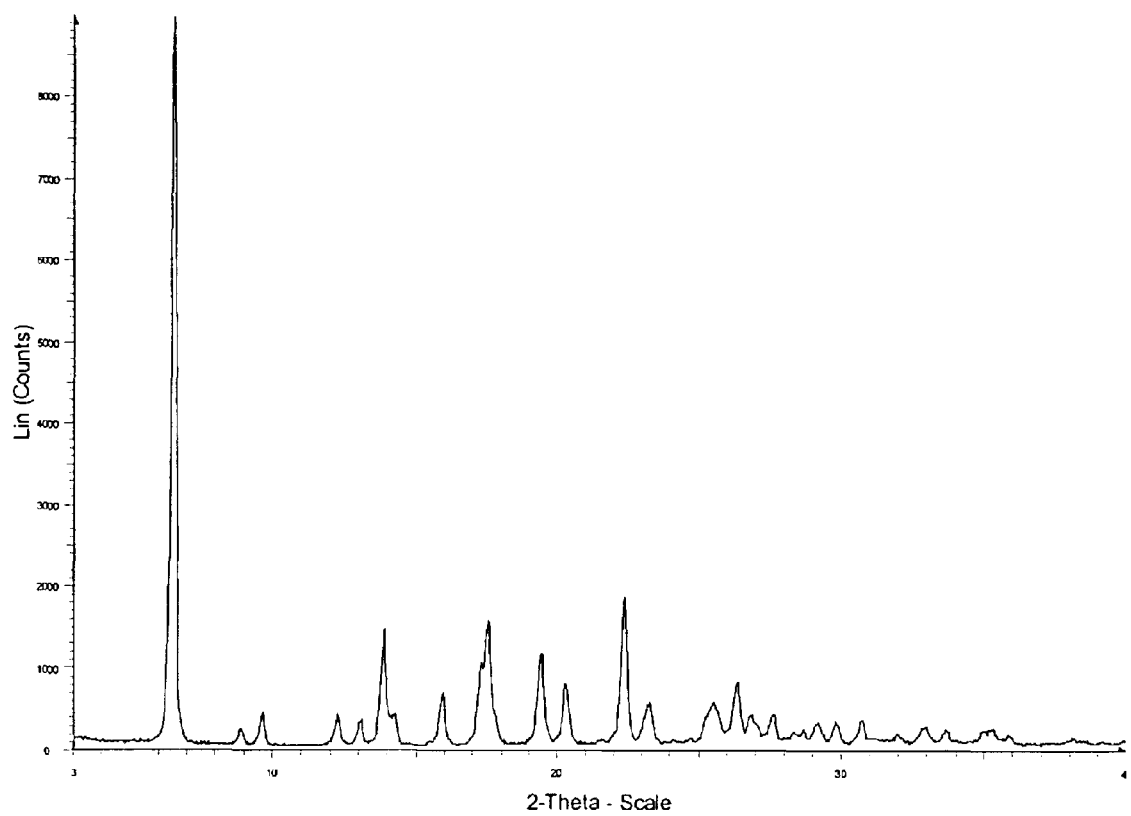
FIG. 8 is the observed powder X-ray diffraction pattern of 3-isopropyl-6-[4-(2,5-difluoro-phenyl)-oxazol-5-yl]-[1,2,4]triazolo[4,3a]pyridine (Form D) (y axis is linear counts per second; X in degrees 2 theta).
Figure 9:
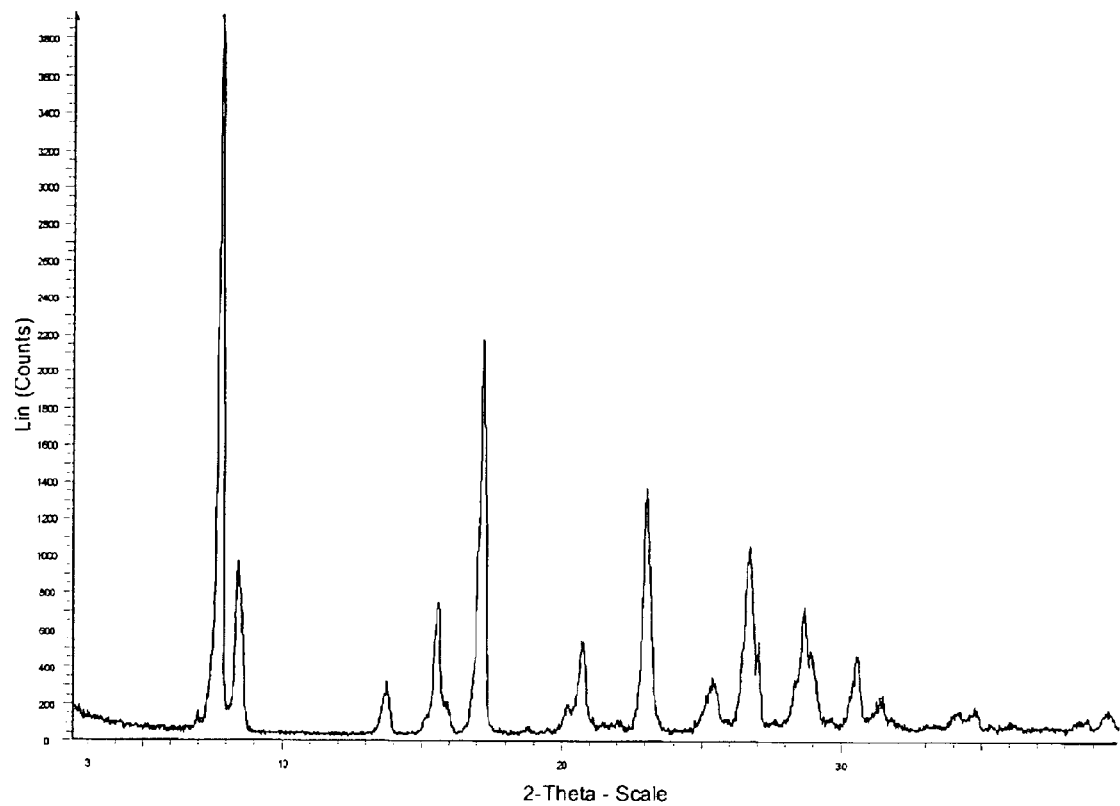
FIG. 9 is the observed powder X-ray diffraction pattern of 3-isopropyl-6-[4-(2,5-difluoro-phenyl)-oxazol-5-yl]-[1,2,4]triazolo[4,3-a]pyridine (Form E) (y axis is linear counts per second; X in degrees 2 theta).
Figure 10:
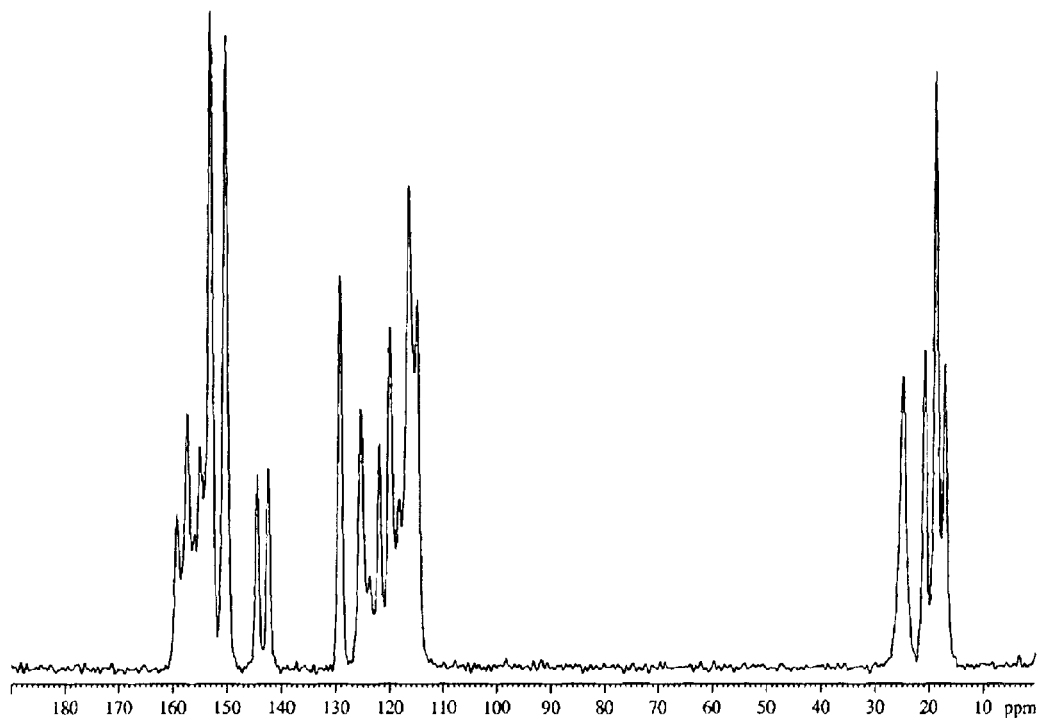
FIG. 10 is the $^{13}C$ NMR spectrum of 3-isopropyl-6-[4-(2,5-difluoro-phenyl)-oxazol-5-yl]-[1,2,4]triazolo[4,3-a]pyridine Form B in the solid phase as measured by cross-polarization magic angle spinning (CPMAS) on a 4 mm BL Bruker wide-bore magic angle spinning (WB MAS) probe positioned in a 11.75 T spectrometer (Bruker Biospin, Inc.) corresponding to 125 Hz $^{13}C$ frequency.
Figure 11:
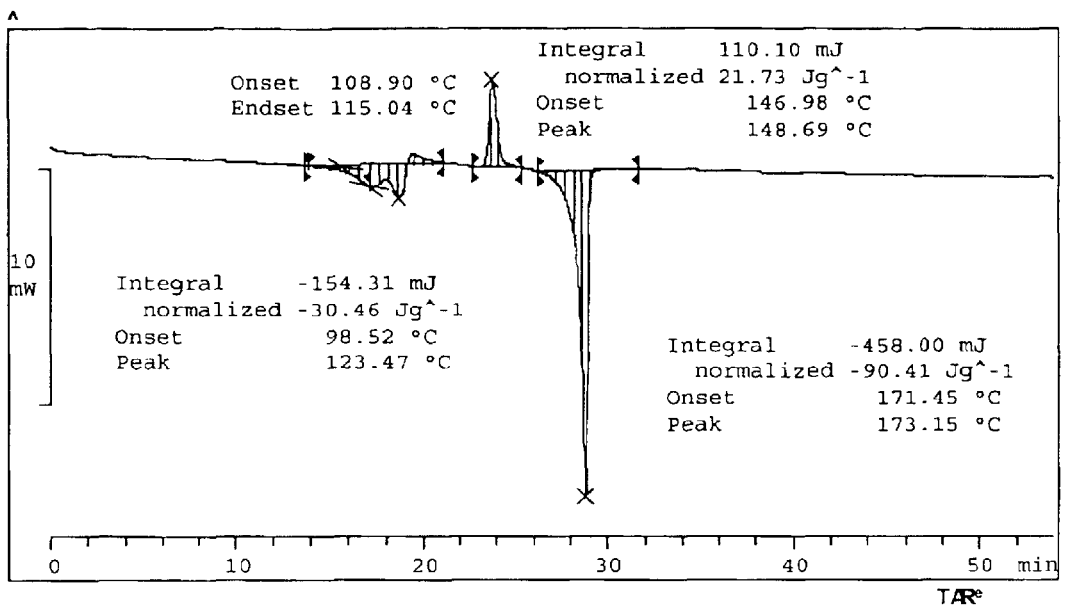
FIG. 11 is a differential scanning calorimetry thermal profile of 3-isopropyl-6-[4-(2,5-difluoro-phenyl)-oxazol-5-yl]-[1,2,4]triazolo[4,3a]pyridine (Form A).
Figure 12:
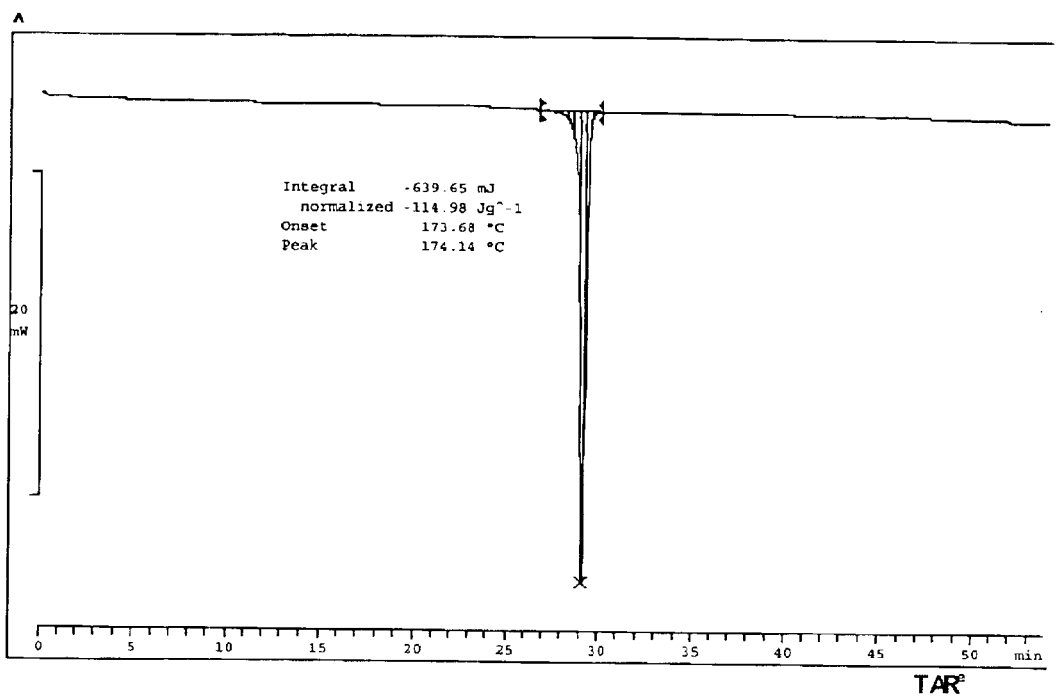
FIG. 12 is a differential scanning calorimetry thermal profile of 3-isopropyl-6-[4-(2,5-difluoro-phenyl)-oxazol-5-yl]-[1,2,4]triazolo[4,3-a]pyridine (Form B).
Figure 13:
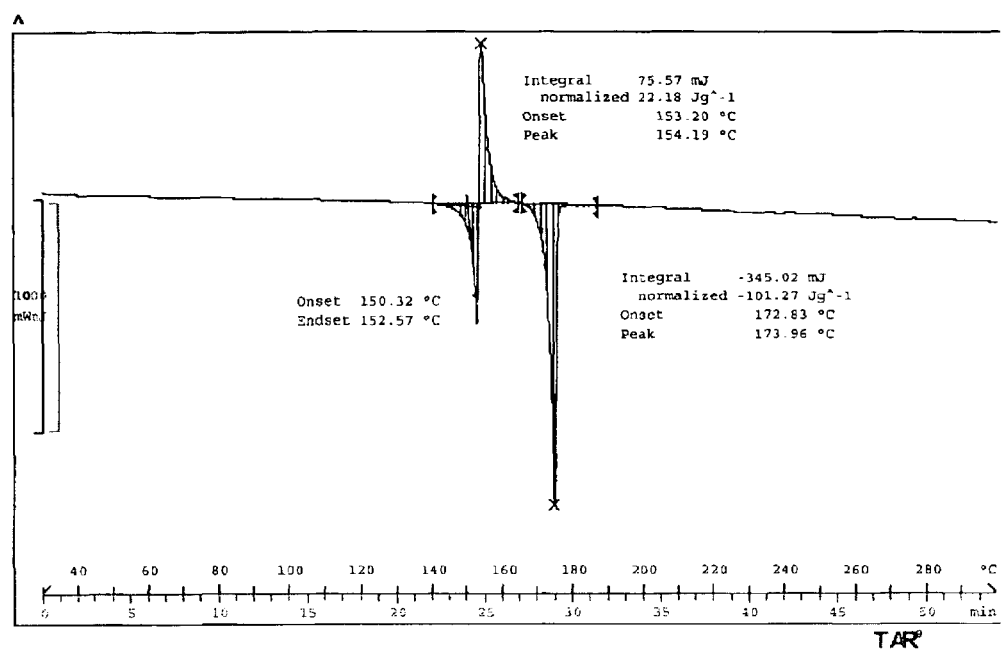
FIG. 13 is a differential scanning calorimetry thermal profile of 3-isopropyl-6-[4-(2,5-difluoro-phenyl)-oxazol-5-yl]-[1,2,4]triazolo[4,3-a]pyridine (Form C).
Figure 14:
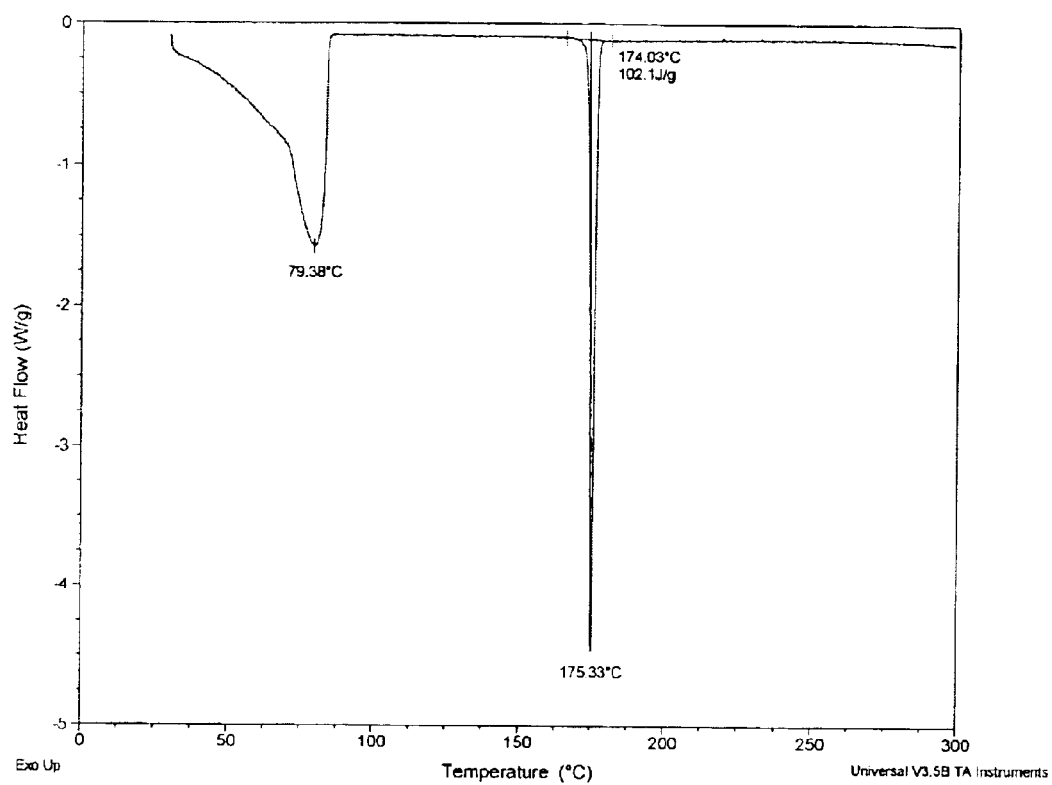
FIG. 14 is a differential scanning calorimetry thermal profile of 3-isopropyl-6-[4-(2,5-difluoro-phenyl)-oxazol-5-yl]-[1,2,4]triazolo[4,3-a]pyridine (Form D).
Figure 15:
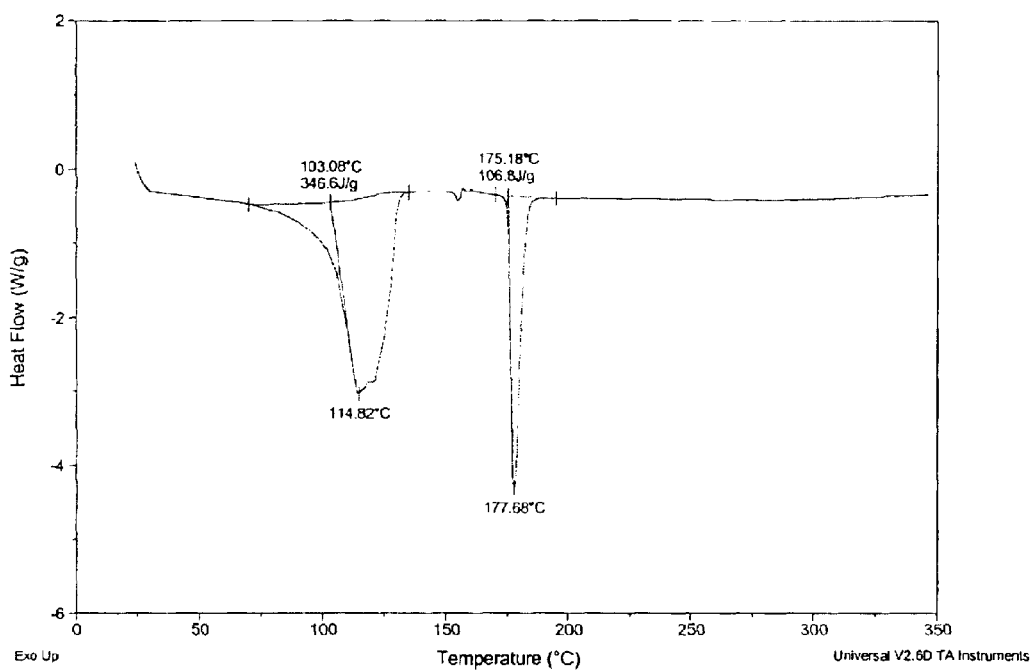
FIG. 15 is a differential scanning calorimetry thermal profile of 3-isopropyl-6-[4-(2,5-difluoro-phenyl)-oxazol-5-yl]-[1,2,4]triazolo[4,3-a]pyridine (Form D).
Figure 16:
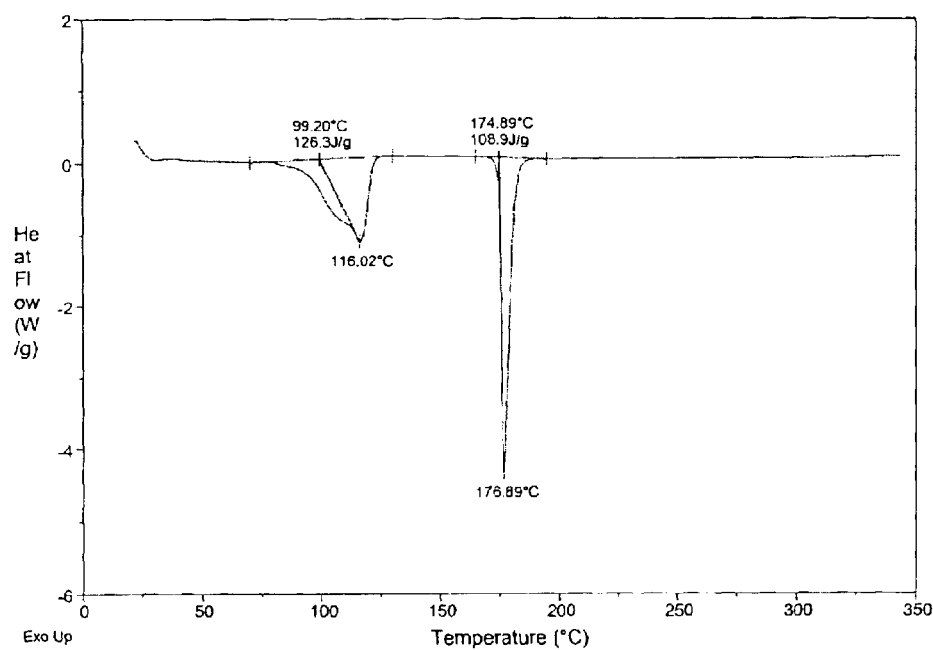
FIG. 16 is a differential scanning calorimetry thermal profile of 3-isopropyl-6-[4-(2,5-difluoro-phenyl)-oxazol-5-yl]-[1,2,4]triazolo[4,3-a]pyridine (Form E).

3-Isopropyl-6-[4-(2,5-difluoro-phenyl)-oxazol-5-yl]-[1,2,4]triazolo-[4,3-a]pyridine may be prepared according to Examples 1 through 13 below.

The activity of 3-isopropyl-6-[4-(2,5-difluoro-phenyl)-oxazol-5-yl]-[1,2,4]triazolo-[4,3-a]pyridine for the various disorders described above can be determined according to one or more of the following assays. 3-Isopropyl-6-[4-(2,5-difluoro-phenyl)-oxazol-5-yl]-[1,2,4]triazolo-[4,3-a]pyridine had an $IC_{50}$ of less than 10 μM in the TNFα and MAPKAP in vitro assays and an $ED_{50}$ of less than 50 mg/kg in the in vivo TNFα assay.

Inhibition of TNF-alpha Production by Human LPS-treated Monocytes

Mononuclear cells are isolated from heparinized blood (1.5 ml of 1000 units/ml heparin for injection, Elkins-Sinn, Inc. added to each 50 ml sample) using Accuspin System-Histopaque-1077 tubes (Sigma A-7054). Thirty-five milliliters of whole blood are added to each tube and the tubes are centrifuged at 2100 rpm for 20 minutes in a Beckman GS-6KR centrifuge with the brake off at room temperature. The mononuclear cells which collect at the interface are removed, diluted with Macrophage serum free medium (Gibco-BRL) (Medium) to achieve a final volume of 50 ml, and collected by centrifugation for 10 minutes. The supernatant is discarded and the cell pellet is washed 2 times with 50 ml of Medium. A sample of the suspended cells is taken before the second wash for counting. Based on this count, the washed cells are diluted with Medium containing 1% FBS to a final concentration of $2.7 \times 10^6$ cells/ml and 75 µl of the cell suspension is added to each well of a 96 well plate.

Compound Preparation 3-isopropyl-6-[4-(2,5-difluoro-phenyl)-oxazol-5-yl]-[1,2,4]triazolo-[4,3-a]pyridine may be tested at final concentrations from 2 µM to 0.016 µM, but may be tested at other concentrations, depending on desire. 3-Isopropyl-6-[4-(2,5-difluoro-phenyl)-oxazol-5-yl]-[1,2,4]triazolo-[4,3-a]pyridine is diluted with DMSO to a final concentration of 2 mM. From this stock solution, 3-isopropyl-6-[4-(2,5-difluoro-phenyl)-oxazol-5-yl]-[1,2,4]triazolo-[4,3-a]pyridine is first diluted 1:25 (5 µl of 2 mM stock+120 µl Medium containing 400 ng/ml LPS and 1% FBS then 40 µl of this dilution is diluted with 360 µl of Medium with LPS. Serial dilutions (1/5) are performed by transferring 20 µl of this dilution to 80 µl of Medium containing both LPS and 0.4% DMSO, resulting in solutions containing 8 µM, 1.6 µM, 0.32 µM and 0.064 µM of 3-isopropyl-6-[4-(2,5-difluoro-phenyl)-oxazol-5-yl]-[1,2,4]triazolo-[4,3-a]pyridine.

Assay

The assay is initiated by adding 25 µl of the diluted 3-isopropyl-6-[4-(2,5-difluoro-phenyl)-oxazol-5-yl]-[1,2,4]triazolo-[4,3-a]pyridine to the mononuclear cell suspension and incubating the cells at 37 C and 5% $CO_2$ for 4 hours.

The 96-well plates are then centrifuged for 10 minutes at 2000 rpm at 4° C. in a Beckman GS-6KR centrifuge to remove cells and cell debris. A 90 µl aliquot of each supernatant is removed and transferred to a 96 well round bottom plate, and this plate is centrifuged a second time to insure that all cell debris is removed. 80 µl of the supernatant is removed and transferred to a new round bottom plate.

Supernatants are analyzed for TNF-α content using R&D ELISA. 25 µl of each sample is added to an ELISA well containing 25 µl of assay diluent RD1F and 75 µl of assay diluent RD5. The assay is run following kit directions except 100 µl of conjugate and substrate solutions are used.

Interpretation

The amount of TNF-α immunoreactivity in the samples is calculated as follows:

% Control=(X-B)/(TOT-B)×100 where X=$OD_{450}$ nm of the test compound well

B=$OD_{450}$ of Reagent Blank wells on the ELISA

Total=$OD_{450}$ of cells that were treated with 0.1% DMSO only.

MAPKAP Kinase-2 Assay

Monocyte preparation

Mononuclear cells are collected from heparinized human blood as detailed above. The washed cells are seeded into 6-well cluster plates at a density of $1 \times 10^7$ cells/well (in 2 ml of Medium). The plates are incubated at 37° C. in a 5% $CO_2$ environment for 2 hours to allow adherence of the monocytes, after which time media supernatants containing non-adherent cells are removed by aspiration and 2 ml of fresh medium are added to each well. Plates are incubated overnight at 37° C. in a 5% $CO_2$ environment.

Cell Activation

Media are removed by aspiration. The attached cells are rinsed twice with fresh Medium, then 2 ml of D-MEM medium containing 10% heat inactivated FBS are added to each well. 3-isopropyl-6-[4-(2,5-difluoro-phenyl)-oxazol-5-yl]-[1,2,4]triazolo-[4,3-a]pyridine is prepared as a 30 mM stock solution in DMSO and diluted to 1250, 250, 50, 10, 2, and 0.4 µM in D-MEM containing 1% DMSO and 10% FBS. To individual wells of the monocyte cultures, 20 µl of these 3-isopropyl-6-[4-(2,5-difluoro-phenyl)-oxazol-5-yl]-[1,2,4]triazolo-[4,3-a]pyridine dilutions are added resulting in final 3-isopropyl-6-[4-(2,5-difluoro-phenyl)-oxazol-5-yl]-[1,2,4]triazolo-[4,3-a]pyridine concentrations of 12.5, 2.5, 0.5, 0.1, 0.02 and 0.004 µM. After a 10 minute preincubation period, 20 µl of a 10 µg/ml LPS solution are added to each well and the plates are incubated at 37° C. for 30 minutes. Media subsequently are removed by aspiration, the attached monocytes are rinsed twice with phosphate buffered saline, then 1 ml of phosphate buffered saline containing 1% Triton X-100 (Lysis Buffer; also containing 1 Complete™ tablet [Boehringer #1697498] per 10 ml of buffer) is added to each well. The plates are incubated on ice for 10 minutes, after which the lysates are harvested and transferred to centrifugation tubes. After all samples are harvested, they are clarified by centrifugation (45,000 rpm for 20 min) and the supernatants recovered.

MAPKAP Kinase-2 Immunoprecipitation

5 µl of anti-MAPKAP kinase-2 antiserum (Upstate Biotechnology #06-534) is added to a microcentrifuge tube (1 tube for each of the above cell lysates) containing 1 ml of a 5% suspension of Protein G-Sepharose (Sigma #P3296) in PBS. These mixtures are incubated for 1 hour at 4° C. (with rocking) after which the beads, containing bound IgG, are recovered by centrifugation and washed twice with 1 ml of 50 mM Tris, pH 7.5, 1 mM EDTA, 1 mM EGTA, 0.5 mM orthovanadate, 0.1% 2-mercaptoethanol, 1% Triton X-100, 5 mM sodium pyrophosphate, 10 mM sodium β-glycerophosphate, 0.1 mM phenylmethylsulfonyl fluoride, 1 µg/ml leupeptin, 1 µg/ml pepstatin, and 50 mM sodium fluoride (Buffer A) by repeated centrifugation. An individual monocyte cell extract (prepared above) is then transferred to each tube containing a pellet of IgG-coated Protein G-Sepharose, and these mixtures are incubated for 2 hours at 4° C. (with rocking). The beads subsequently are harvested by centrifugation, and the resulting bead pellets are washed once with 0.5 ml of Buffer A containing 0.5 M NaCl, once with 0.5 ml of Buffer A, and once with 0.1 ml of a buffer composed of 20 mM MOPS, pH 7.2, 25 mM sodium β-glycerophosphate 5 mM EGTA, 1 mM orthovanadate, and 1 mM dithiothreitol (Buffer B).

MAPKAP Kinase-2 Activity Assessment

A kinase reaction mixture stock is prepared as follows: 2.2 µl of 10 mCi/ml γ[$^{32}$P]ATP, 88 µl of 1.3 µg/ml solution of MAPKAP Kinase-2 substrate peptide (Upstate Biotechnology #12-240), 11 µl of 10 mM ATP, 8.8 µl of 1 M $MgCl_2$, and 770 µl of Buffer B. To each of the immune complex-Protein G-pellets, 40 µl of the kinase reaction mixture is added and the tubes are incubated for 30 minutes at 30° C. The tubes then are clarified by centrifugation and 25 µl of each supernatant is spotted onto a P81 filter paper disk (Whatman #3698-023). After allowing all fluid to soak into the filter, each disk is placed into an individual well of 6-well cluster plates and the filters are washed sequentially with 2 ml of 0.75% phosphoric acid (3 washes/15 min each) and once with acetone (10 minutes). The filters then are air dried and transferred to liquid scintillation vials containing 5 ml of scintillation fluid. Radioactivity is determined in a liquid scintillation counter. The amount of radioactivity bound to the filter at each test agent concentration is expressed as a percentage of that observed from cells stimulated with LPS in the absence of a test agent.

In Vivo Inhibition of TNFα

Rats were weighed and dosed with vehicle (0.5% methyl cellulose, Sigma) or drug. One hour later, animals were injected i.p. with LPS (50 ug/rat, Sigma L-4130). Ninety minutes later, animals were sacrificed by asphyxiation with $CO_2$ and bled by cardiac puncture. Blood was collected in Vaccutainer tubes and spun for 20 minutes at 3000 rpm. Serum was assayed for TNFα levels using an ELISA (R&D Systems).

This invention also encompasses pharmaceutical compositions containing and methods of treating or preventing comprising administering prodrugs of 3-isopropyl-6-[4-(2,5-difluoro-phenyl)-oxazol-5-yl]-[1,2,4]triazolo-[4,3-a]pyridine. 3-Isopropyl-6-[4-(2,5-difluoro-phenyl)-oxazol-5-yl]-[1,2,4]triazolo-[4,3-a]pyridine can be converted into prodrugs. Prodrugs include compounds wherein an amino acid residue, or a polypeptide chain of two or more (e.g., two, three or four) amino acid residues which are covalently joined through peptide bonds to free amino groups of 3-isopropyl-6-[4-(2,5-difluoro-phenyl)-oxazol-5-yl]-[1,2,4]triazolo-[4,3-a]pyridine. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above amino substituents of 3-isopropyl-6-[4-(2,5-difluoro-phenyl)-oxazol-5-yl]-[1,2,4]triazolo-[4,3-a]pyridine through the carbonyl carbon prodrug sidechain.

The compositions of the present invention may be formulated in a conventional manner using one or more pharmaceutically acceptable carriers. Thus, 3-isopropyl-6-[4-(2,5-difluoro-phenyl)-oxazol-5-yl]-[1,2,4]triazolo-[4,3-a]pyridine may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use.

Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

3-Isopropyl-6-[4-(2,5-difluoro-phenyl)-oxazol-5-yl]-[1,2,4]triazolo-[4,3-a]pyridine can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

3-Isopropyl-6-[4-(2,5-difluoro-phenyl)-oxazol-5-yl]-[1,2,4]triazolo-[4,3-a]pyridine may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, 3-isopropyl-6-[4-(2,5-difluoro-phenyl)-oxazol-5-yl]-[1,2,4]triazolo-[4,3-a]pyridine may be in powder form for reconstitution with a suitable vehicle, e.g., sterile pyrogen-free water, before use.

3-Isopropyl-6-[4-(2,5-difluoro-phenyl)-oxazol-5-yl]-[1,2,4]triazolo-[4,3-a]pyridine may also be formulated in rectal compositions such as suppositories or retention enemas, e.g., containing conventional suppository bases such as cocoa butter or other glycerides.

For intranasal administration or administration by inhalation, 3-isopropyl-6-[4-(2,5-difluoro-phenyl)-oxazol-5-yl]-[1,2,4]triazolo-[4,3-a]pyridine may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of 3-isopropyl-6-[4-(2,5-difluoro-phenyl)-oxazol-5-yl]-[1,2,4]triazolo-[4,3-a]pyridine for oral, parenteral or buccal administration to the average adult human for the treatment of the conditions referred to above (e.g., inflammation) is 0.1 to 200 mg of 3-isopropyl-6-[4-(2,5-difluoro-phenyl)-oxazol-5-yl]-[1,2,4]triazolo-[4,3-a]pyridine per unit dose which could be administered, for example, 1 to 4 times per day. Preferably, for once a day dosing 250 mg of 3-isopropyl-6-[4-(2,5-difluoro-phenyl)-oxazol-5-yl]-[1,2,4]triazolo-[4,3-a]pyridine could be administered.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, for example 2, 3, 4 or 8 times, giving for example, 1, 2 or 3 doses each time.

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonirile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 amu to 1100 amu. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

One of ordinary skill in the art will appreciate that in some cases, protecting groups may be required during preparation. After the target molecule is prepared, the protecting group can be removed by methods well known to those of ordinary skill in the art, such as described in Greene and Wuts, *Protective Groups in Organic Synthesis*, (2$^{nd}$ Ed., John Wiley & Sons, 1991).

Thermal Analysis

Differential Scanning Calorimetry (DSC) analysis was carried out on either TA Instruments DSC2920 or TA instrument Q1000 or a Mettler DSC 821, calibrated with indium. DSC sample was prepared by weighing 2–4 mg of material in an aluminum pan with a pinhole. The sample was heated under nitrogen, at a rate of 5° C. or 10° C. per minute from 3 to 300 C.

Power X-ray Diffraction Analysis

The experimental conditions under which the powder X-ray diffraction was conducted are as follows: Cu anode; wavelength 1: 1.54056; wavelength 2: 1.54439 (Rel Intensity: 0.500); range #1-coupled: 3.000 to 40.000; step size: 0.040; step time: 1.00; smoothing width: 0.300; and threshold: 1.0.

Single Crystal X-ray Analysis

Data was collected at room temperature using Bruker X-ray diffractometers equipped with copper radiation and graphite monochromators. Structures were solved using direct methods. The SHELXTL computer library provided by Bruker AXS, Inc facilitated all necessary crystallographic computations and molecular displays.

Calculation of PXRD Pattern from Single Crystal Data

The single crystal structural data provide the cell dimensions, space group and atomic positions of a crystal form. These parameters are used as the basis to calculate a perfect powder pattern of that crystal form. The calculation can be done using SHELXTL Plus computer program, Reference Manual by Siemens Analytical X-ray Instrument, Chapter 10, p. 179–181, 1990. Comparing the calculated PXRD pattern and the experimental pattern will confirm whether a powder sample corresponds to an assigned single crystal structure. This procedure has been performed on the crystal form B and a match between the two patterns indicates the agreement between powder sample and the corresponding single crystal structure.

$^{13}$C Solid-state NMR Method

All $^{13}$C solid state NMR spectra were collected on 11.75 T spectrometer (Bruker Biospin, Inc., Billerica, Mass.), corresponding to 125 MHz $^{13}$C frequency. The spectra were acquired using cross-polarization magic angle spinning (CPMAS) probe operating at ambient temperature and pressure. 4 mm BL Bruker probes was employed, accommodating 75 mg of sample with maximum speed of 15 kHz. Data were processed with exponential line broadening function of 5.0 Hz. Proton decoupling of 100 kHz was used. Sufficient number of acquisitions were averaged out to obtain adequate signal-to-noise ratios for all peaks. Typically, 1500 scans were acquired with recycle delay of 4.5 s, corresponding to approximately 2 hour total acquisition time. Magic angle was adjusted using KBr powder according to standard NMR vendor practices. The spectra were referenced relative to the upfield resonance of adamantane (ADMNT) at 29.5 ppm. The spectral window minimally included the spectra region from 220 to −10 ppm.

$^{13}$C chemical shifts between 0 to 50 ppm and 110 to 180 ppm can be used to identify the crystal form in a tablet.

Preparation 1

5-Bromo-pyridin-2-yl-hydrazine

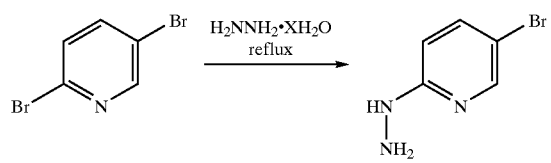

A 12 L three-necked round-bottomed flask equipped with a mechanical stirrer and a condenser, connected on top with a nitrogen bubbler and a thermometer, was charged with 2,5-dibromopyridine (442 g, 1.87 moles), hydrazine hydrate (55% wt., 1057 ml, 18.7 moles), poly(ethylene glycol) (average M$_n$ about 300, 1.87 L), 2-butanol (373 ml) and water (1.87 L). The mixture was heated at reflux for 29 hours. The heating source was removed and the mixture was stirred for an additional 20 hours. To the resulting slurry, cold water (2.2 L) was added. The slurry was stirred for an additional 30 minutes and filtered. The cake was washed with cold water (3×200 ml) and dried in a vacuum-oven (40° C.) for 48 hours. The title compound was obtained as off-white flakes (305 g, yield 87%).

GCMS(m/z): 187 (M+). H$^1$ NMR (400 MHz, CDCl$_3$): δ 8.14 (d, J=2.0 Hz, 1H), 7.55 (dd, J=8.7/2.0 Hz, 1H), 6.66 (d, J=8.7 Hz, 1H), 5.89 (brs, 1H), 3.65 (brs, 2H).

Preparation 2

6-Bromo-3-isopropyl-[1,2,4]triazolo(4,3-a)pyridine hydrochloride

Step 2

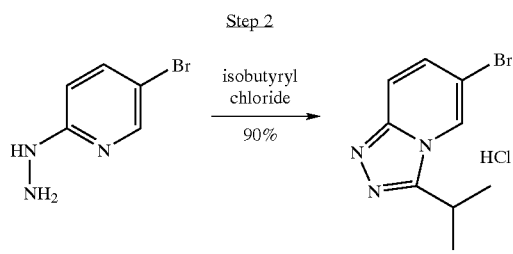

A 500 ml three-necked round-bottomed flask equipped with a mechanical stirrer and a condenser, connected on top to a nitrogen bubbler and a thermometer, was charged with 5-bromo-pyridin-2-yl-hydrazine (43.4 g, 0.231 moles) and isobutyryl chloride (218 ml, 2.08 moles). The mixture was gently refluxed for 3 hours. The heating source was then replaced with an ice-water bath and the slurry cooled to room temperature. Hexane (220 ml) was added and the slurry stirred at room temperature for 15 minutes and filtered. The cake was washed with hexane (3×70 ml) and then dried in a vacuum-oven (35° C.) for 48 hours. The title compound was obtained as an off-white powder (58.96 g, yield 92.3%).

Preparation 3

6-Bromo-3-isopropyl-[1,2,4]triazolo(4,3-a)pyridine

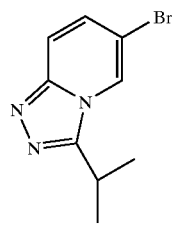

A 5 L three-necked round-bottomed flask, equipped with a mechanical stirrer and a thermometer, was charged with 6-bromo-3-isopropyl-[1,2,4]triazolo(4,3-a)pyridine hydrochloride (587.0 g, 2.12 moles), water (1.2 L) and dichloromethane (1.8 L). The biphasic mixture was cooled to 5 to 10° C. using an ice-water bath. Sodium hydroxide (1N aqueous solution) (2.15 L) was added over a period of 10 minutes. The mixture was stirred in the bath for 15 minutes. The organic layer was then isolated and the aqueous layer extracted with dichloromethane (600 mL). The combined organic extracts are washed with 1:1 brine-water (2 L) and dried (MgSO$_4$). Most of dichloromethane was removed by rotary evaporation. Ethyl acetate (800 ml) was then added. After removing about 400 ml of solvents, hexane (3.2 L) was added. The slurry was stirred in an ice-water bath for 2 hours and then filtered. The cake was washed with 9:1 hexane-ethyl acetate (3×150 ml) and dried in a vacuum-oven (30–35° C.) for 18 hours. The title compound (471.6 g, yield 92.5%), was obtained as a tan sandy powder.

H$^1$ NMR (400 MHz, CDCl$_3$): δ 8.06 (s, 1H), 7.64 (d, J=9.5 Hz, 1H), 7.24 (d, J=9.5 Hz, 1H), 3.33 (m, J=7.0 Hz, 1H), 1.52 (d, J=7.0 Hz, 6H).

Preparation 4

3-Isopropyl-[1,2,4]triazolo(4,3-a)-6-pyridinecarboxaldehyde

Step 3

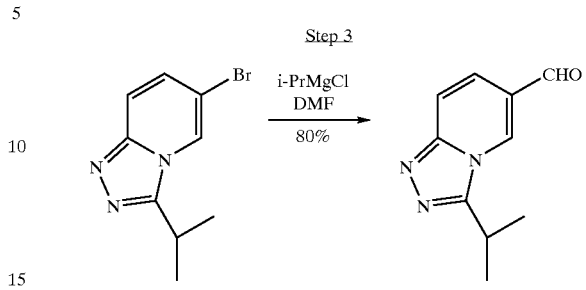

A 12 L three-necked round-bottomed flask, equipped with a mechanical stirrer, an addition funnel and a thermometer, was charged with 6-bromo-3-isopropyl-[1,2,4]triazolo(4,3-a)pyridine (200.0 g, 0.833 moles) and tetrahydrofuran (J. T. Baker, low water 2.0 L). The solution was cooled to −8° C. using an acetone/dry ice bath. A solution of isopropylmagnesium chloride in tetrahydrofuran (2.0M, 500 ml, 1.0 mole) L) was added via the addition funnel over a period of 55 minutes. The resulting brownish slurry was stirred between −4 to 0° C. for 30 minutes. Dimethylformamide (Aldrich, anhydrous, 155 ml, 2.0 moles) was added via an addition funnel over a period of 5 minutes. The cooling bath was replaced with a heating mantle and the addition funnel was replaced with a condenser. The slurry was heated to 55° C. and stirred at this temperature for 2 hours. The reaction mixture was cooled to 15° C. and dichloromethane (3 L) was added. The slurry was slowly poured into a stirred and ice-water cooled (15° C.) 10% by weight aqueous solution of citric acid (3 kg) over a period of 5 minutes. The biphasic mixture was stirred at 17 to 20° C. for 30 minutes. The organic layer was then isolated and the aqueous layer extracted with dichloromethane (5×1 L). The combined organic extracts were washed with 1:1 v/v brine-water (2 L), dried (MgSO$_4$) and concentrated. To the brownish residual solid was added ethyl acetate (800 ml). The slurry was stirred at room temperature for 10 minutes at which time hexane (800 ml) was added. The slurry was stirred at room temperature for 2 more hours and filtered. The cake was washed with 1:1 v/v hexane-ethyl acetate (3×150 ml) and dried in a vacuum-oven (30–35° C.) for 18 hours. The title compound was obtained as a yellowish sandy powder (126.6 g, yield 80%).

GCMS(m/z): 189 (M+). H$^1$ NMR (400 MHz, CDCl$_3$): δ 10.00 (s, 1H), 8.49 (s, 1H), 7.79 (d, J=9.5 Hz, 1H), 7.68 (d, J=9.5 Hz, 1H), 3.47 (m, J=7.0 Hz, 1H), 1.56 (d, J=7.0 Hz, 6H),

Preparation 5

P-toluenesulfinic acid

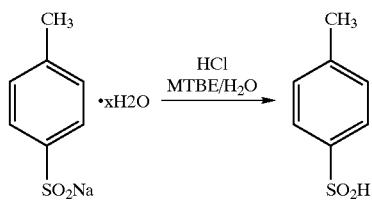

A 5 L three-necked round-bottomed flask, equipped with a mechanical stirrer and a thermometer, was charged with p-toluenesulfinic acid, sodium salt hydrate (Aldrich, CH₃C₆H₄SO₂Na.xH₂O, 392.0 g), tap water (2 L) and methyl t-butyl ether (2 L). The mixture was stirred at room temperature for 10 minutes at which time hydrochloric acid (37% wt. in water, 142 ml, 1.2 moles) was added over a period of 5 minutes. The biphasic mixture was stirred at room temperature for 30 minutes. The organic layer was then isolated and the aqueous layer extracted with methyl t-butyl ether (500 mL). The combined organic extracts were concentrated to a residual white semi-solid, which was diluted with toluene (700 ml). Most of solvents were removed and hexane (1.8 L) was then added. The slurry was stirred at room temperature for 30 minutes and filtered. The cake was washed with hexane (2×300 ml) and dried in a vacuum-oven (30–35° C.) for 3 hours. The product, p-toluenesulfinic acid (240.0 g), was obtained as a white powder.

Preparation 6

N-[(2.5-difluoro-phenyl)-(toluene-4-sulphonyl)-methyl]-formamide

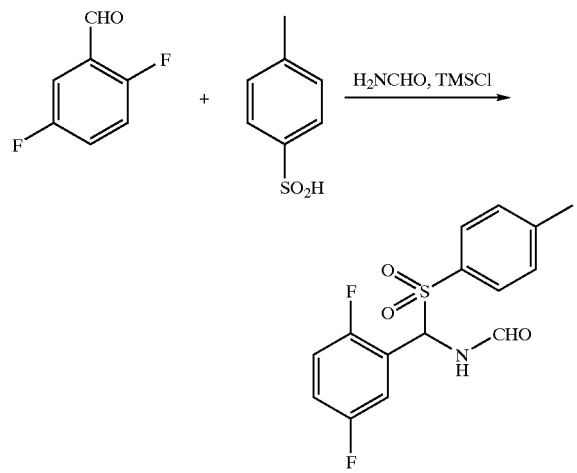

A 5 L three-necked round-bottomed flask, equipped with a mechanical stirrer, a condenser and a thermometer, was charged with 2,5-difluorobenzaldehyde (142.11 g, 1 mole). Toluene (500 ml), acetonitrile (500 ml), formamide (99.3 ml, 2.5 moles) and chlorotrimethylsilane (139.6 ml, 1.1 moles) were added respectively. The cloudy mixture was heated to 50° C. and stirred at this temperature for 7 hours. p-Toluenesulfinic acid (218.68 g, 1.4 moles) was added. The mixture was stirred at 50° C. for 6 hours and then 13 hours at room temperature. Methyl t-butyl ether (1.8 L) and water (1.7 L) were then added. The mixture was stirred at room temperature for 15 minutes at which time the organic layer was separated. The aqueous layer was extracted with methyl t-butyl ether (500 ml). Most of the solvents were removed from the combined organic extracts. To the residual white semi-solid, hexane (1 L) and water (1 L) were added. The slurry was stirred at room temperature for 30 minutes and filtered. The cake was washed with hexane (2×200 ml) and dried in a vacuum-oven (30° C.) for 18 hours. The product, N-[(2,5-Difluoro-phenyl)-(toluene-4-sulfonyl)-methyl]-formamide (258.3 g, yield 79%,), was obtained as a white powder.

Preparation 7

[α-(P-toluenesulphonyl)-2,5-difluorobenzyl] isonitrile

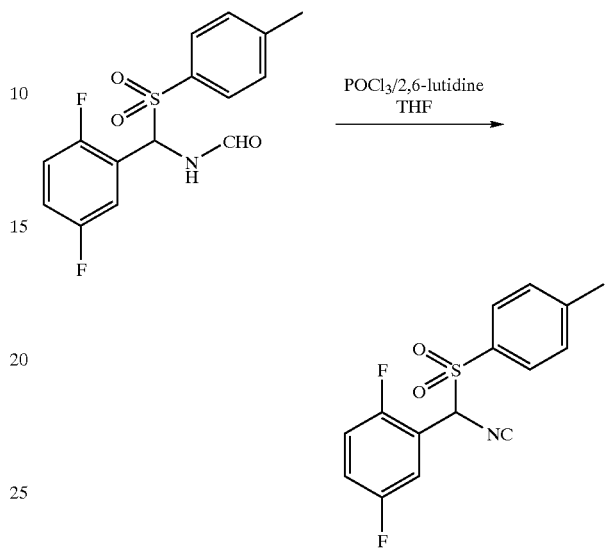

A 5 L three-necked round-bottomed flask, equipped with a mechanical stirrer, an addition funnel and a thermometer, was charged with N-[(2,5-Difluoro-phenyl)-(toluene-4-sulfonyl)-methyl]-formamide (207.0 g, 0.636 moles) and tetrahydrofuran (J. T. Baker, low water, 1.5 L). Phosphorous oxychloride (118.6 ml, 1.27 moles) was quickly poured into the reaction mixture (less than 5 minutes). The mixture was stirred at room temperature for 10 minutes and then cooled to 4° C. using an ice/water bath. 2,6-Lutidine (445 ml, 3.82 moles) was added via the addition funnel over a period of 30 minutes. The cooling bath was then removed and the mixture was stirred at room temperature for 18 hours. The reaction mixture was poured into a stirred and ice-water cooled solution of 1.5 kg of ice and 1.1 L of saturated aqueous sodium bicarbonate (NaHCO₃). The mixture was then extracted with ethyl acetate (2 L plus 1.5 L). The combined organic extracts were washed with 1N aqueous hydrochloric acid (3 L), saturated aqueous NaHCO₃ (3 L) and brine (3 L); and then dried (MgSO4). After removing all solvents, isopropanol (1.8 L) was added to the residual brownish solid. The resulting slurry was stirred at room temperature for 2 hours. Water (0.9 L) was added and the slurry was stirred for additional 30 minutes at room temperature and then filtered. The cake was washed with 2:1 isopropanol-water (2×500 ml) and dried in a vacuum-oven (30° C.) for 48 hours. The product, [α-(p-Toluenesulfonyl)-2,5-difluorobenzyl]isonitrile (133.4 g, yield 68%,), was obtained as a brownish powder.

H¹ NMR (400 MHz, CDCl₃): δ, 7.7 (d, J=8.3 Hz, 2H) 7.41 (d, J=8.3 Hz, 2H), 7.18 (m, 3H), 5.91 (s, 1H), 2.50 (s. 3H).

Preparation 8

[α-(P-toluenesulphonyl)-2,5-difluorobenzyl] isonitrile

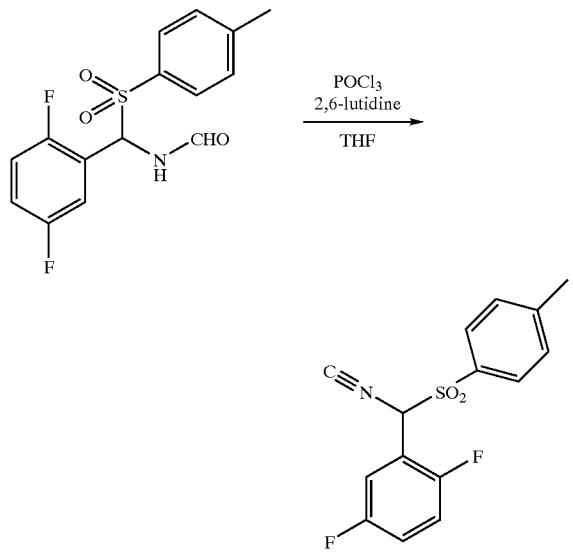

To a clean a dry nitrogen purged acetone boiled out 100 gallon glass lined reactor was charged, 7.9 Kg of N-[(2,5-Difluoro-phenyl)-(toluene-4-sulfonyl)-methyl]-formamide (24, moles), 16 gallons of tetrahydrofuran and 7.8 Kg of phosphorous oxychloride (51 moles). The batch was allowed to stir at 20° C. for 30 minutes and then cooled to 3.5° C. To the batch was added 15.8 Kg of 2,6-lutidine (146 moles) over 15 minutes. The reaction mixture was allowed to warm to 23° C. and was stirred for 17 hours at 23° C. The reaction was judged complete by HPLC and was charged to a 40 gallon solution of 10% sodium bicarbonate at 22° C., and the contents were allowed to stir for 30 minutes. To the batch was then added 25 gallons of ethyl acetate and the layers were separated. The water layer was backwashed with 9 gallons of ethyl acetate and the product rich ethyl acetate combined with the first wash. The product rich ethyl acetate layers were added to a 10% citric acid solution (20 gallons) and then stirred. The organic layer was checked by HPLC for 2,6 lutidine and then separated. The organic layer was washed with 10 gallons of saturated NaCl and dried over 7.9 Kg of magnesium sulfate. The drying agents were removed by filtration and the cake was washed with 4 gallons of ethyl acetate. The ethyl acetate layer was concentrated to 7 gallons under vacuum at an internal temperature of 24° C. The batch was then added to 11 gallons of IPO at 21° C. and allowed to granulate at 4° C. for 12 hours. The product was isolated via filtration and washed with 4 gallons of 5° C. IPO. The product was then dried at 34° C. for 22 hours with nitrogen bleed to recover 5.0 Kg of the title compound (66% yield).

Preparation 9

6-[Oxazol-5-yl]-3-isopropyl-[1,2,4]triazolo[4,3-a]pyridine

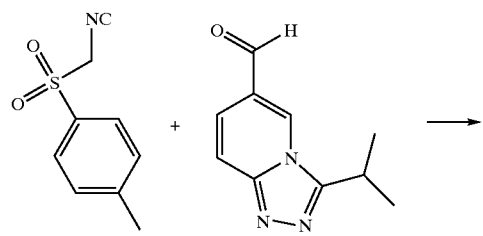

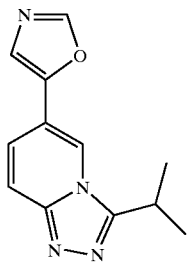

To a clean dry 5 liter round bottomed flask equipped with a mechanical stirrer, nitrogen bubbler, heating mantle, temperature controller, and condenser, was charged 3-isopropyl-[1,2,4]triazolo(4,3-a)-6-pyridinecarboxaldehyde (140.9 grams, 0.745 moles), potassium carbonate (133.8 grams, 0.968 moles), tosylmethyl isocyanide (146.9 grams, 0.745 moles),and methanol (2114 ml). This mixture was heated at reflux and stirred for 1.5 to 2.0 hours at 65 to 70° C. Assay by HPLC showed the reaction to be complete. The pot was concentrated atmospherically to about one third of original volume. Water (1409 ml), was added and the pot further concentrated to a pot temperature of 65 to 66° C. to remove the remaining methanol. After cooling, the desired product was extracted with methylene chloride (1409 ml). The extraction was repeated twice with methylene chloride (2 times 705 ml). The combined extracts were atmospherically concentrated and displaced with Isopropyl alcohol (420 ml). A thick slurry formed. Hexanes (1690 ml) were added and the slurry allowed to granulate for 12 to 16 hours at 20 to 25° C. The solids were collected by vacuum filtration, washed with hexanes, and dried to yield 111.45 grams, 97.8% purity (HPLC), 65.5% of theory.

$^1$H NMR (CDCl$_3$, 400 MHz) δ 8.23 (s, 1H), 7.98 (s, 1H), 7.82 (d, 1H, J=9.5 Hz), 7.46–7.43 (m, 2H), 3.43 (sept, 1H, J=7.05 Hz), 1.56 (d, 6H, J=7.05 Hz); MS 229 (M$^+$+1).

Preparation 10

6-[4-Bromo-oxazol-5-yl]-3-isopropyl-[1,2,4]triazolo[4,3-a]pyridine

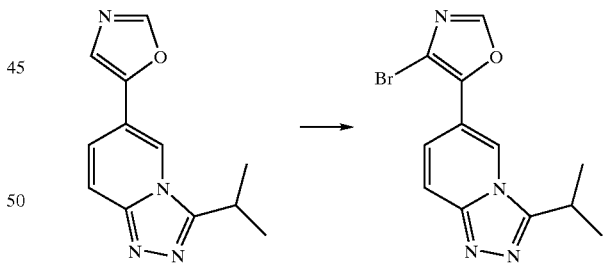

A clean, dry, 1 liter 4 neck round bottom flask equipped with mechanical stirrer, temperature probe, and purged with nitrogen, was charged with 6-[oxazol-5-yl]-3-isopropyl-[1,2,4]triazolo[4,3-a]pyridine (45.2 grams 0.198 moles) and dimethylformamide (271 ml). The pot was cooled below −60° C. with a dry ice/acetone bath. Lithium bis(trimethylsilyl)amide, 1 molar solution in tetrahydrofuran (198 ml 0.198 moles), was added, keeping the temperature below −60° C. After the addition was complete, the pot was further cooled to below −70° C. and stirred for 1 hour. While stirring, a solution of N-bromosuccinimide (35.24 g 0.198 moles) and dimethylformamide (105 ml), were stirred in a separate 500 ml round bottom flask under nitrogen. After the one hour stir at −70° C., the solution of N-bromosuccinimide and dimethylformamide was slowly added to the anion keeping the temperature below −70° C. After the addition, the reaction was continued for one hour below −70° C. The batch was then warmed to room temperature and quenched into methylene chloride (452 ml) and 1N sodium hydroxide (452 ml). The organic layer was then separated. The aqueous layer was extracted a second time with methylene chloride (135 ml). The combined organic phase was washed with 1N sodium hydroxide (452 ml) and saturated brine solution (452 ml). The organic phase was then dried over magnesium sulfate (50 grams) and concentrated/displaced with isopropyl ether (226 ml) to a temperature of 42° C. A thick slurry formed upon cooling. The solids were granulated at 20 to 25° C. for two hours, filtered, washed with isopropyl ether (50 ml), and dried to afford 53.0 grams of light yellow solids, 96.4% purity (HPLC), 87% of theory.

$^1$H NMR (CDCl$_3$, 400 MHz) δ 8.56 (s, 1H), 7.95 (s, 1H), 7.85 (d, 1H, J=9.5 Hz), 7.77 (d, 1H, J=9.5 Hz), 3.43 (sept, 1H, J=7.05 Hz), 1.56 (d, 6H, J=7.05 Hz); MS: 310, 309, 308, 307 (M$^+$+1).

EXAMPLE 1

6-[4-(2,5-Difluoro-phenyl)-oxazol-5-yl]-3-isopropyl-[1,2,4]triazolo-[4,3-a]pyridine

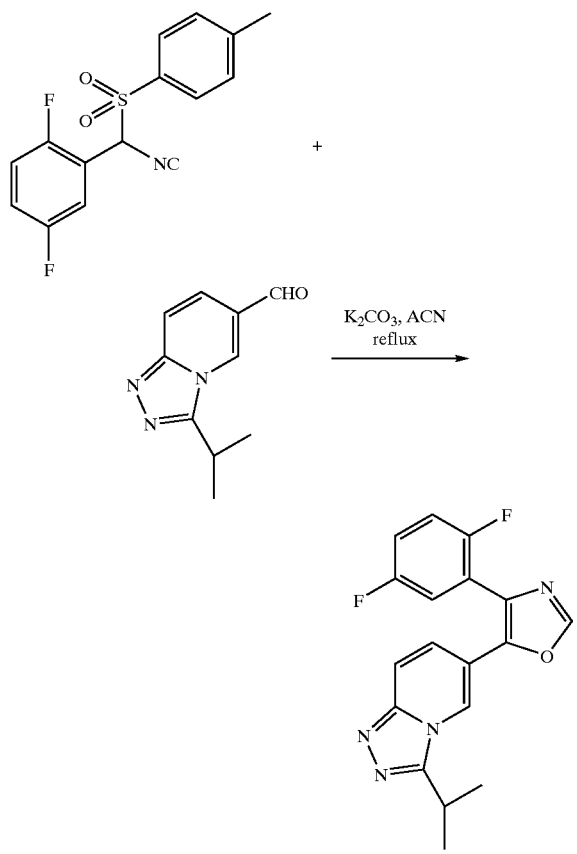

A 5 L three-necked round-bottomed flask, equipped with a mechanical stirrer, a condenser and a thermometer, was charged with N-α-tosyl-(2,5-difluorobenzyl)-isocyanide (179.4 g, 0.584 moles), 3-isopropyl-[1,2,4]triazolo(4,3-a)-6-pyridinecarboxaldehyde (110.46 g, 0.584 moles), potassium carbonate (Aldrich, <325 mesh, 104.88 g, 0.759 moles) and acetonitrile (1.75 L). The mixture was heated at reflux and stirred for 22 hours. The reaction mixture was then cooled to room temperature and poured into a stirred solution of 2 kg of ice and 5 kg of water. The resulting slurry was stirred at room temperature for 2 hours and filtered. The brownish solid was washed with water (2×500 ml) and dried in a vacuum-oven (30° C.) for 48 hours. The crude product (180 g) was purified over a silica gel column (1.1 kg) and eluted with 1:1 ethyl acetate-hexane (to remove less polar impurities), ethyl acetate and finally 20:1 ethyl acetate-methanol. The fractions containing mainly the product were combined and concentrated to small volume (about 600 ml). The resulting slurry was filtered. The cake was washed with ethyl acetate and dried in a vacuum-oven (30° C.) for 18 hours. The light brownish powder (142 g) was further purified by recrystallization from isopropanol (800 ml). 6-[4-(2,6-Difluoro-phenyl)-oxazol-5-yl]-3-isopropyl-[1,2,4]triazolo[4,3-a]pyridine was obtained as a light-tan powder (142.1 g, yield 61%).

Melting point 175.7–176.2° C. Elemental analysis, found: C 63.54%, H 4.08%, N 16.56; Analytical calculated for: C 63.52%, H 4.15%, N 16.46%. LCMS (m/z): 341 (M+1). $^1$HNMR (400 MHz, CDCl$_3$): δ 8.18 (s, 1H), 8.12 (s, 1H), 7.89 (d, 1H, J=9.6 Hz), 7.46–7.51 (m, 1H), 7.37 (d, 1H J=9.6 Hz), 7.05–7.1 (m, 2H), 3.30–3.33 (m, 1H), 1.48 (d, 6H, J=7.1 Hz).

EXAMPLE 2

6-[4-(2,5-Difluoro-phenyl)-oxazol-5-yl]-3-isopropyl-[1,2,4]triazolo[4,3-a]pyridine hydrogen chloride Crude 6-[4-(2,5-difluoro-phenyl)-oxazol-5-yl]-3-isopropyl-[1,2,4]triazolo[4,3-a]pyridine (5.0 g) was dissolved in isopropanol (40 ml). Hydrochloric acid (13.3% weight) in isopropanol (4.4 g) was added. The resulting slurry was stirred at room temperature for 30 minutes and filtered. The cake was washed with isopropanol and dried in a vacuum oven (80° C.) for 2 hours. 6-[4-(2,5-Difluoro-phenyl)-oxazol-5-yl]-3-isopropyl-[1,2,4]triazolo[4,3-a]pyridine hydrogen chloride was obtained as an off-white solid (2.8 g, yield 50%).

$^1$HNMR (400 MHz, CDCl$_3$): δ 8.49 (d, J=9.5 Hz, 1H), 8.38 (s, 1H), 8.16 (s, 1H), 7.90 (d, J=9.5 Hz, 1H), 7.49–7.53 (m, 1H), 7.13–7.23 (m, 2H), 3.43–3.50 (m, 1H), 1.55 (d, J=7.1 Hz, 6H).

EXAMPLE 3

6-[4-(2,5-Difluoro-phenyl)-oxazol-5-yl]-3-isopropyl-[1,2,4]triazolo-[4,3-a]pyridine methanesulfonate 6-[4-(2,5-Difluoro-phenyl)-oxazol-5-yl]-3-isopropyl-[1,2,4]triazolo[4,3-a]pyridine (5.10 g, 15 mmol) was dissolved in isopropanol (25 ml). A solution of methanesulfonic acid (1.44 g, 15 mmol) in isopropanol (15 ml) was added. The resulting slurry was stirred at room temperature for 3 hours and filtered. The cake was washed with isopropanol and dried in a vacuum oven (80° C.) for 4 hours. 6-[4-(2,5-Difluoro-phenyl)-oxazol-5-yl]-3-isopropyl-[1,2,4]triazolo[4,3-a]pyridine methanesulfonate was obtained as an off-white powder (6.03 g, yield 92%).

$^1$HNMR (400 MHz, CDCl$_3$): δ 8.67 (d, J=9.5 Hz, 1H), 8.38 (s, 1H), 8.15 (s, 1H), 7.83 (d, J=9.5 Hz, 1H), 7.46–7.50

(m, 1H), 7.13–7.22 (m, 2H), 3.44–3.51 (m, 1H), 2.86 (s, 3H), 1.54 (d, J=7.1 Hz, 6H).

EXAMPLE 4

6-[4-(2,5-Difluoro-phenyl)-oxazol-5-yl]-3-isopropyl-[1,2,4]triazolo-[4,3-a]pyridine p-toluenesulfonate To 6-[4-(2,5-Difluoro-phenyl)-oxazol-5-yl]-3-isopropyl-[1,2,4]triazolo[4,3-a]pyridine (5.0 g, 15 mmol) slurried in acetone (50 ml) was added p-Toluenesulfonic acid (2.7 g, 15 mmol). The resulting slurry was heated to 50° C. to form a solution and was then cooled and stirred at room temperature for 12 hours and filtered. 6-[4-(2,5-Difluoro-phenyl)-oxazol-5-yl]-3-isopropyl-[1,2,4]triazolo[4,3-a]pyridine p-toluenesulfonate was obtained.

EXAMPLE 5

6-[4-(2,5-Difluoro-phenyl)-oxazol-5-yl]-3-isopropyl-[1,2,4]triazolo-[4,3-a]pyridine sulfate To 6-[4-(2,5-Difluoro-phenyl)-oxazol-5-yl]-3-isopropyl-[1,2,4]triazolo[4,3-a]pyridine (5.0 g, 15 mmol) slurried in acetone (50 ml) was added sulfuric acid (850 μl). The resulting slurry was heated to reflux to form a solution and was then cooled and stirred at room temperature for 12 hours and filtered to yield 4.2 grams of 6-[4-(2,5-Difluoro-phenyl)-oxazol-5-yl]-3-isopropyl-[1,2,4]triazolo[4,3-a]pyridine p-toluenesulfonate.

EXAMPLE 6

3-Isopropyl-6-[4-(2,5-difluoro-phenyl)-oxazol-5-yl]-[1,2,4]triazolo-[4,3-a]pyridine

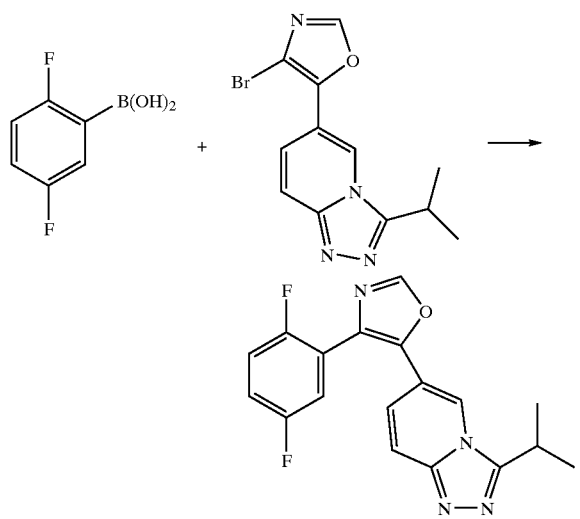

6-[4-bromo-oxazol-5-yl]-3-isopropyl-[1,2,4]triazolo[4,3-a]pyridine (33.0 grams, 0.107 moles), difluorophenylboronic acid (25.34 grams, 0.1605 moles), Pd(PPh$_3$)$_4$ (12.36 grams, 0.0107 moles), triethylamine (22.37 ml, 0.1605 moles), 2B ethanol (495 ml) and water (33 ml), were added to a 2 liter 4 neck round bottom flask (equipped with mechanical stirring, nitrogen, heating mantle, temperature controller, and a condenser). The batch was stirred while heating to 65 to 70° C. The reaction was stirred overnight at about 70° C. Additional difluorophenylboronic acid (8.5 grams, 0.054 moles) and triethylamine (7.53 ml, 0.054 moles), were added and the reaction was allowed to proceed overnight at 70° C. Additional difluorophenylboronic acid (8.5 grams, 0.054 moles) and triethylamine (7.53 ml, 0.054 moles), were added and the reaction was allowed to proceed overnight once again at 70° C. Toluene (30 ml) was added and the reaction was allowed to go overnight once again at 70° C. The reaction sample showed no more starting material by HPLC. Water (495 ml) was added to the batch and the pot granulated for 4 hours at 20 to 25° C. The solids were collected by vacuum filtration, washed with 2 B ethanol/water 50:50 (25 ml of each), and dried in a vacuum oven at 45° C. for 4 hours under full vacuum to afford 14.4 grams of the title compound (40.6% yield, 93.4% purity by HPLC).

EXAMPLE 7

3-Isopropyl-6-[4-(2,5-difluoro-phenyl)-oxazol-5-yl]-[1,2,4]triazolo-[4,3-a]pyridine

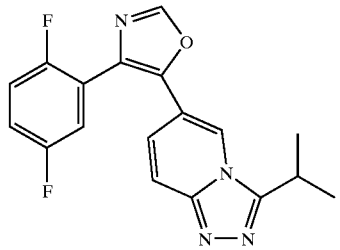

Crude 3-isopropyl-6-[4-(2,5-difluoro-phenyl)-oxazol-5-yl]-[1,2,4]triazolo[4,3-a]pyridine (5.0 grams), Darco G-60 carbon (500 mg), and isopropyl alcohol (30 ml), were heated to 80° C. in a single neck 100 ml round bottom flask. The solution was allowed to cool to 60° C. and filtered over Filter-aid® to remove carbon. The cake was washed with isopropyl alcohol (30 ml), then allowed to further cool to 20 to 25° C. and granulate overnight. The solids were collected by vacuum filtration, washed with isopropyl alcohol (10 ml), and dried to afford 4.2 grams of the title compound, 98.8% purity (HPLC), 84% yield.

EXAMPLE 8

3-Isopropyl-6-[4-(2,5-difluoro-phenyl)-oxazol-5-yl]-[1,2,4]triazolo-[4,3-a]pyridine form A

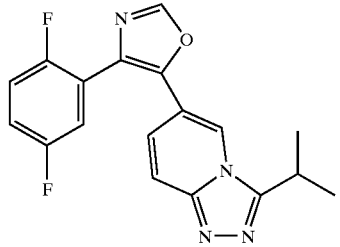

3-Isopropyl-6-[4-(2,5-difluoro-phenyl)-oxazol-5-yl]-[1,2,4]triazolo[4,3-a]pyridine (37.0 grams), triturated in 1:1 ethyl acetate/hexane (300 ml) at 20 to 23° C. The suspension was filtered and the cake was washed with 1:1 ethyl acetate/hexane and dried in a vacuum oven at 40° C. for 48 hours to afford 37.0 grams of crystal form A.

TABLE 1

List of Powder X-ray Diffraction peaks - Form A (±0.2°)

| Calculated Angle 2-Theta ° | Relative Intensity %[1] | Experimental Angle 2-Theta ° | Relative Intensity %[1] |
|---|---|---|---|
| 6.9 | 69.2 | 6.9 | 44.7 |
| 9.1 | 100 | 9.1 | 100 |
| 10.9 | 25.5 | 10.9 | 27.7 |
| 13.4 | 2.9 | 13.3 | 3.1 |
| 13.8 | 9.7 | 13.8 | 63.5 |
| 15.2 | 4.8 | 15.1 | 8.5 |
| 16.3 | 6.4 | 16.3 | 14.4 |
| 17.0 | 22.9 | 16.9 | 31.3 |
| 17.4 | 21 | 17.3 | 95.1 |
| 18.1 | 5.6 | 18.1 | 15 |
| 18.4 | 4.1 | 18.3 | 11.6 |
| 19.3 | 1.4 | 19.4 | 3.7 |
| 20.0 | 7.8 | 19.9 | 19.7 |
| 20.3 | 14 | 20.3 | 39.7 |
| 20.7 | 6.5 | 20.8 | 10 |
| 21.2 | 1 | 21.6 | 4.6 |
| 22.0 | 5.9 | 22.0 | 13.2 |
| 22.6 | 32.1 | 22.5 | 61.9 |
| 23.6 | 5.9 | 23.5 | 19.8 |
| 24.4 | 2.3 | 24.4 | 7 |
| 24.8 | 0.7 | 24.8 | 5 |
| 25.6 | 8.4 | 25.5 | 23.8 |
| 26.6 | 13.8 | 26.5 | 23.6 |
| 27.1 | 8.5 | 27.0 | 27.3 |
| 27.7 | 11.6 | 27.6 | 29.7 |
| 28.0 | 9.6 | 27.9 | 32.4 |
| 28.5 | 1.3 | 28.5 | 5.9 |
| 29.0 | 7.3 | 29.1 | 18.7 |
| 29.9 | 1.4 | 29.9 | 8.4 |
| 30.5 | 5 | 30.6 | 12.6 |
| 30.9 | 2.4 | 30.7 | 15.8 |
| 31.7 | 3.6 | 31.6 | 15.3 |
| 32.3 | 2.8 | 32.4 | 6.9 |
| 32.8 | 2.1 | 32.8 | 5.1 |
| 33.2 | 0.6 | 33.2 | 3.4 |
| 34.5 | 2 | 34.5 | 6 |
| 35.2 | 0.8 | 36.0 | 4.8 |
| 35.9 | 1.2 | 36.7 | 8.6 |
| 36.1 | 0.8 | 37.6 | 3.8 |
| 36.7 | 1.5 | 38.2 | 2.9 |
| 38.8 | 0.6 | 38.8 | 3.5 |
| 39.3 | 1.5 | 39.3 | 5.4 |

[1]The relative intensities may change depending on the crystal size and morphology.

TABLE 2

X-ray crystallographic data from single crystal of Form A

| | Form A |
|---|---|
| Empirical formula | $C_{18}H_{14}N_4OF_2$ |
| Formula weight | 340.33 |
| Temperature (K) | 268 (2) |
| Crystal size (mm) | 0.04 × 0.06 × 0.15 |
| Space group | $P2_1/n$ monoclinic |
| Unit cell dimensions | a = 6.6546 (11) Å |
| | b = 25.675 (4) Å |
| | C = 10.5455 (17) Å |
| | α = 90° |
| | β = 98.918 (5)° |
| | γ = 90° |
| Z (per formula) | 4 |
| Density (g/cm³) | 1.270 |
| R | 0.0783 |

This is a single crystal structure of anhydrous which produced a PXRD pattern matched with that of Form A, an ethylacetate solvate; the single crystal is a desolvated solvate as Form A.

EXAMPLE 9

3-Isopropyl-6-[4-(2,5-difluoro-phenyl)-oxazol-5-yl]-[1,2,4]triazolo-[4,3-a]pyridine form B

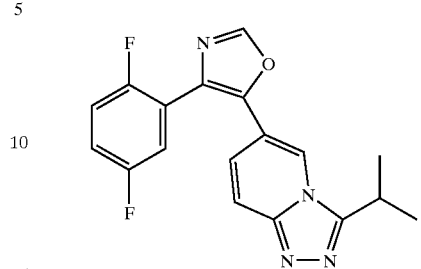

Pure 3-isopropyl-6-[4-(2,5-difluoro-phenyl)-oxazol-5-yl]-[1,2,4]triazolo[4,3-a]pyridine (3.4 grams), and acetone (41 ml) were heated to 50 to 55° C. until a clear golden solution was achieved. The heat was removed and the solution was allowed to cool, (approximately 35 to 40° C.), and granulate overnight at 20 to 25° C. The solids were collected by vacuum filtration, washed with acetone (7 ml), and dried to afford 2.38 grams of crystal form B, 99.6% purity (HPLC), 70% yield.

TABLE 3

List of Powder X-ray Diffraction peaks - Form B (±0.2°)

| Calculated[1] Angle 2-Theta ° | Relative Intensity %[2] | Experimental Angle 2-Theta ° | Relative Intensity %[2] |
|---|---|---|---|
| 8.5 | 96.1 | 8.6 | 60 |
| 10.3 | 28.7 | 10.3 | 14.4 |
| 11.2 | 52.8 | 11.2 | 28.2 |
| 11.9 | 8.3 | 11.9 | 4.4 |
| 12.3 | 4.2 | 12.4 | 3.6 |
| 12.9 | 5.1 | 13.0 | 3.9 |
| 13.5 | 4.4 | 13.5 | 3.8 |
| 14.8 | 100 | 14.9 | 33.7 |
| 15.3 | 20.7 | 15.3 | 19.2 |
| 16.5 | 20.3 | 16.6 | 10 |
| 16.9 | 83.5 | 17.0 | 39.3 |
| 17.1 | 55.5 | 17.2 | 39.2 |
| 17.4 | 26.4 | 18.2 | 20 |
| 18.2 | 30.7 | 18.5 | 4.6 |
| 18.5 | 7.2 | 19.0 | 18.3 |
| 19.0 | 30 | 19.4 | 8.8 |
| 19.3 | 16.6 | 19.7 | 36.8 |
| 19.7 | 50.8 | 20.3 | 9.2 |
| 20.2 | 14.7 | 20.8 | 23.2 |
| 20.7 | 39.4 | 21.2 | 7 |
| 21.1 | 11.5 | 21.8 | 33.5 |
| 21.8 | 51.1 | 22.4 | 70.7 |
| 22.3 | 76.7 | 23.1 | 7.8 |
| 23.0 | 8.6 | 23.8 | 6 |
| 23.7 | 7.2 | 24.1 | 7.5 |
| 24.0 | 11.9 | 24.5 | 8.8 |
| 24.4 | 10.5 | 24.9 | 15.3 |
| 24.8 | 22 | 25.5 | 8 |
| 25.4 | 22.9 | 26.0 | 39.5 |
| 26.0 | 65.9 | 26.4 | 19 |
| 26.4 | 40.6 | 26.7 | 25.6 |
| 26.7 | 36.1 | 27.2 | 10.6 |
| 27.2 | 14.6 | 28.0 | 100 |
| 27.9 | 70 | 28.5 | 26.1 |
| 28.4 | 32.9 | 28.9 | 13.9 |
| 28.8 | 17.2 | 29.3 | 11.8 |
| 29.2 | 15 | 30.2 | 4.6 |
| 30.0 | 8.7 | 30.3 | 5.4 |
| 30.3 | 6.6 | 30.9 | 7.1 |
| 30.9 | 12.4 | 31.8 | 3.7 |
| 31.4 | 4.1 | 32.3 | 5.4 |
| 31.7 | 4.5 | 33.7 | 6.8 |

TABLE 3-continued

List of Powder X-ray Diffraction peaks - Form B (±0.2°)

| Calculated[1] Angle 2-Theta ° | Relative Intensity %[2] | Experimental Angle 2-Theta ° | Relative Intensity %[2] |
|---|---|---|---|
| 32.2 | 11.5 | 34.7 | 3.4 |
| 32.9 | 5.5 | 35.3 | 3.5 |
| 33.7 | 5.3 | 36.0 | 4.1 |
| <u>34.1</u> | <u>4.1</u> | | |
| <u>35.0</u> | <u>4.5</u> | | |
| 35.3 | 4.1 | | |
| 36.0 | 3.7 | | |

[1]Peak underlined were not listed in the experimental pattern because either it has low intensity of less than 4% or unresolved within ±0.2° 2 theta.
[2]The relative intensities may change depending on the crystal size and morphology.

TABLE 4

X-ray crystallographic data from single crystal Form B

| | Form B |
|---|---|
| Empirical formula | $C_{18}H_{14}N_4OF_2$ |
| Formula weight | 340.33 |
| Temperature (K) | 298 (2) |
| Crystal size (mm) | 0.10 × 0.20 × 0.24 |
| Space group | $P2_1/c$ monoclinic |
| Unit cell dimensions | a = 20.7164 (6) Å |
| | b = 10.7621 (3) Å |
| | c = 14.3522 (4) Å |
| | α = 90° |
| | β = 92.1490 (10)° |
| | γ = 90° |
| Z (per formula) | 8 |
| Density (g/cm³) | 1.414 |
| R | 0.0450 |

TABLE 5

$^{13}C$ ss-NMR chemical shifts of Form B (±0.2 ppm)

| |
|---|
| 159.2 |
| 157.2 |
| 156.0 |
| 154.9 |
| 153.0 |
| 150.2 |
| 144.4 |
| 142.4 |
| 129.2 |
| 125.3 |
| 123.7 |
| 121.9 |
| 112.0 |
| 118.3 |
| 116.4 |
| 114.9 |
| 24.8 |
| 20.8 |
| 18.7 |
| 17.0 |

EXAMPLE 10

3-Isopropyl-6-[4-(2,5-difluoro-phenyl)-oxazol-5-yl]-[1,2,4]triazolo-[4,3-a]pyridine form C

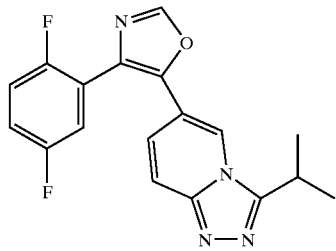

The product of Example 8 was further dried in a vacuum oven at 100° C. for 4 hours to produce crystal form C.

Form C was also produced as either pure Form C or as a mixed pattern from both fast and slow evaporations in ethyl acetate and IPA, fast evaporations in and toluene, and slow evaporations in chloroform, dichloromethane, IPA, MEK, and 95:5 (v/v) IPA/water.

TABLE 6

List of Powder X-ray Diffraction peaks - Form C (±0.2°)

| Form C Angle 2-Theta ° | Relative Intensity %* |
|---|---|
| 6.4 | 6.2 |
| 7.4 | 99.5 |
| 8.5 | 2.6 |
| 11.1 | 15.4 |
| 11.6 | 15.8 |
| 12.8 | 40.8 |
| 13.3 | 28.4 |
| 14.8 | 38.6 |
| 16.3 | 5.6 |
| 17.3 | 9.8 |
| 17.7 | 16.3 |
| 18.2 | 13 |
| 18.8 | 25.5 |
| 19.6 | 100 |
| 20.3 | 20 |
| 21.0 | 16.2 |
| 21.3 | 23.9 |
| 22.0 | 31.7 |
| 22.3 | 68.3 |
| 22.9 | 21.4 |
| 23.4 | 10.9 |
| 24.0 | 8.2 |
| 24.9 | 9.4 |
| 25.7 | 38.5 |
| 26.4 | 15.3 |
| 26.8 | 56.8 |
| 27.9 | 16.8 |
| 28.7 | 9.7 |
| 29.4 | 7.3 |
| 29.9 | 11.2 |
| 30.7 | 12.8 |
| 31.4 | 9.6 |
| 31.7 | 8.5 |
| 32.4 | 7.4 |
| 34.3 | 6.4 |
| 36.9 | 4.7 |
| 37.7 | 4.8 |

*The relative intensities may change depending on the crystal size and morphology.

EXAMPLE 11

3-Isopropyl-6-[4-(2,5-difluoro-phenyl)-oxazol-5-yl]-[1,2,4]triazolo-[4,3-a]pyridine form D

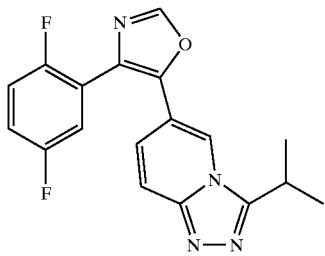

3-Isopropyl-6-[4-(2,5-difluoro-phenyl)-oxazol-5-yl]-[1,2,4]triazolo[4,3-a]pyridine (300 mg), was suspended in 10 ml of 0.1% methyl cellulose for 12 hours at 20 to 25° C. The solids were collected by vacuum filtration, and air dried for four hours to afford 300 mg of crystal form D.

Form D was also obtained a slurry in water, 1:1 (v/v) methanol/water, and 9:1 (v/v) acetonitrile/water at ambient and 60° C. or methylcellulose suspension. It is a unstable hydrate, a dihydrate by powder sample (~10% water by weight) and a trihydrate (14.7% water by weight) by single crystal data. Since dehydration occurs between 30 to 70° C., drying or standing at ambient condition may cause partial decomposition.

TABLE 7

List of Powder X-ray Diffraction peaks - Form D (±0.2°)

| Calculated[1] Angle 2-Theta ° | Relative Intensity %[2] | Experimental Angle 2-Theta ° | Relative Intensity %[2] |
|---|---|---|---|
| 6.6 | 100 | 6.5 | 100 |
| 8.9 | 6.7 | 8.9 | 2.8 |
| 9.7 | 5.1 | 9.6 | 4.8 |
| 12.3 | 7.1 | 12.2 | 4.6 |
| 13.1 | 2.4 | 13.0 | 4 |
| 13.9 | 13.7 | 13.8 | 16.1 |
| 14.3 | 16.4 | 14.2 | 4.5 |
| 15.6 | 2.1 | 15.4 | 1.1 |
| 16.0 | 22.7 | 15.9 | 7.6 |
| 17.3 | 28.6 | 17.3 | 11.7 |
| 17.6 | 28.8 | 17.5 | 17.4 |
| 19.5 | 10.6 | 19.4 | 12.9 |
| 20.4 | 17.8 | 20.3 | 8.9 |
| 21.7 | 2.2 | 21.6 | 1.3 |
| 22.5 | 44.4 | 22.4 | 20.6 |
| 23.3 | 12.9 | 23.2 | 6.3 |
| 24.2 | 1.8 | 24.7 | 1.5 |
| 24.8 | 2.1 | 25.3 | 4.6 |
| 25.3 | 12.9 | 25.5 | 6.3 |
| 25.6 | 26.8 | 26.3 | 9.1 |
| <u>26.1</u> | <u>8.1</u> | 26.8 | 4.6 |
| 26.4 | 29.7 | 27.6 | 4.7 |
| 26.9 | 9.9 | 28.3 | 2.4 |
| <u>27.2</u> | <u>12.9</u> | 28.7 | 2.6 |
| 27.7 | 9.7 | 29.2 | 3.7 |
| 28.2 | 3.9 | 29.8 | 3.8 |
| 28.5 | 9.5 | 30.7 | 4 |
| 28.8 | 8.7 | 32.0 | 2.2 |
| 29.3 | 8.7 | 32.9 | 2.9 |
| 29.9 | 5.5 | 33.7 | 2.8 |
| 30.8 | 7.3 | 35.0 | 2.6 |
| <u>31.3</u> | <u>3.1</u> | 35.3 | 2.7 |
| <u>31.5</u> | <u>3.6</u> | 35.9 | 2 |
| 32.1 | 3.2 | 38.2 | 1.6 |
| 33.1 | 6.4 | 38.6 | 1.2 |
| 33.8 | 4.2 | | |

TABLE 7-continued

List of Powder X-ray Diffraction peaks - Form D (±0.2°)

| Calculated[1] Angle 2-Theta ° | Relative Intensity %[2] | Experimental Angle 2-Theta ° | Relative Intensity %[2] |
|---|---|---|---|
| 35.1 | 6.9 | | |
| 35.4 | 5.9 | | |
| 36.0 | 2.6 | | |
| 38.3 | 3 | | |
| 38.6 | 2 | | |

[1]Peak underlined were not listed in the experimental pattern because either it has low intensity of less than 4% or unresolved within ±0.2° 2 theta.
[2]The relative intensities may change depending on the crystal size and morphology.

TABLE 8

X-ray crystallographic data from single crystal Form D

| | Form D |
|---|---|
| Empirical formula | $C_{18}H_{14}N_4OF_2 \cdot 3H_2O$ |
| Formula weight | 394.38 |
| Temperature (K) | 298 (2) |
| Crystal size (mm) | 0.40 × 0.28 × 0.10 |
| Space group | $P2_1/n$ monoclinic |
| Unit cell dimensions | a = 15.1326 (17) Å |
| | b = 6.9630 (8) Å |
| | c = 19.229 (2) Å |
| | α = 90° |
| | β = 108.087 (2)° |
| | γ = 90° |
| Z (per formula) | 4 |
| Density (g/cm$^3$) | 1.360 |
| R | 0.0471 |

EXAMPLE 12

3-Isopropyl-6-[4-(2,5-difluoro-phenyl)-oxazol-5-yl]-[1,2,4]triazolo-[4,3-a]pyridine form E

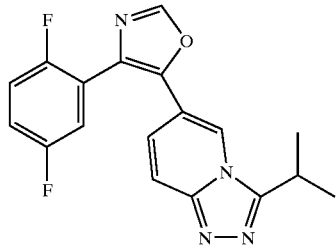

3-Isopropyl-6-[4-(2,5-difluoro-phenyl)-oxazol-5-yl]-[1,2,4]triazolo[4,3-a]pyridine (39 grams), and ethanol (3.2 ml) were sonicated at 20 to 23° C. until a clear golden solution was achieved. The solution was filtered through a 0.2 micron filter. After slow evaporation (6 days) to dryness, crystal form E (39 mg) was produced.

Form E has been identified from XRPD analysis of 95:5 (v/v) IPA/water slow cool and fast evaporations, an IPA/water slow cool and from an ethanol slow evaporation. It is a monohydrate that dehydrates between 75 to 100° C. and converts to Form B upon dehydration.

TABLE 9

List of Powder X-ray Diffraction peaks - Form E (±0.2°)

| Form E Angle 2-Theta ° | Relative Intensity %* |
|---|---|
| 7.7 | 100 |
| 8.4 | 24.3 |
| 13.7 | 8.5 |
| 15.5 | 19.9 |
| 15.9 | 5.5 |
| 17.2 | 57.3 |
| 20.2 | 5.2 |
| 20.7 | 14.2 |
| 23.0 | 36.5 |
| 25.4 | 9.2 |
| 26.7 | 28.2 |
| 27.0 | 14.1 |
| 28.4 | 8.8 |
| 28.6 | 19.4 |
| 28.9 | 12.9 |
| 30.5 | 12.2 |
| 31.4 | 5.8 |
| 34.8 | 5.1 |

*The relative intensities may change depending on the crystal size and morphology.

EXAMPLE 13

3-Isopropyl-6-[4-(2,5-difluoro-phenyl)-oxazol-5-yl]-[1,2,4]triazolo-[4,3-a]pyridine

Tablet Formulation:

| Ingredient | Amount (mg) |
|---|---|
| 3-isopropyl-6-[4-(2,5-difluoro-phenyl)-oxazol-5-yl]-[1,2,4]triazolo[4,3-a]pyridine | 50 |
| Lactose | 50 |
| Cornstarch (for mix) | 10 |
| Cornstarch (paste) | 10 |
| Magnesium stearate (1%) | 5 |
| Total | 125 |

3-Isopropyl-6-[4-(2,5-difluoro-phenyl)-oxazol-5-yl]-[1,2,4]triazolo[4,3-a]pyridine, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for inhibiting cartilage damage or treating osteoarthritis.

What is claimed is:

1. The crystalline form of the compound 3-isopropyl-6-[4-(2,5-difluoro-phenyl)-oxazol-5-yl]-[1,2,4]triazolo[4,3-a]pyridine having the single crystal x-ray crystallographic data.

| Form A | |
|---|---|
| Empirical formula | $C_{18}H_{14}N_4OF_2$ |
| Formula weight | 340.33 |
| Temperature (K) | 268 (2) |
| Crystal size (mm) | 0.04 × 0.06 × 0.15 |
| Space group | $P2_1/n$ monoclinic |
| Unit cell dimensions | a = 6.6546 (11) Å |
| | b = 25.675 (4) Å |
| | c = 10.5455 (17) Å |
| | α = 90° |
| | β = 98.918 (5)° |
| | γ = 90° |
| Z (per formula) | 4 |
| Density (g/cm³) | 1.270 |
| R | 0.0783 |

2. The crystalline form of the compound 3-isopropyl-6-[4-(2,5-difluoro-phenyl)-oxazol-5-yl]-[1,2,4]triazolo[4,3-a]pyridine having the single crystal x-ray crystallographic data.

| Form B | |
|---|---|
| Empirical formula | $C_{18}H_{14}N_4OF_2$ |
| Formula weight | 340.33 |
| Temperature (K) | 298 (2) |
| Crystal size (mm) | 0.10 × 0.20 × 0.24 |
| Space group | $P2_1/c$ monoclinic |
| Unit cell dimensions | a = 20.7164 (6) Å |
| | b = 10.7621 (3) Å |
| | c = 14.3522 (4) Å |
| | α = 90° |
| | β = 92.1490 (10)° |
| | γ = 90° |
| Z (per formula) | 8 |
| Density (g/cm³) | 1.414 |
| R | 0.0450 |

3. The crystalline form of the compound 3-isopropyl-6-[4-(2,5-difluoro-phenyl)-oxazol-5-yl]-[1,2,4]triazolo[4,3-a]pyridine having the single crystal x-ray crystallographic data.

| Form D | |
|---|---|
| Empirical formula | $C_{18}H_{14}N_4OF_2 \cdot 3H_2O$ |
| Formula weight | 394.38 |
| Temperature (K) | 298 (2) |
| Crystal size (mm) | 0.40 × 0.28 × 0.10 |
| Space group | $P2_1/n$ monoclinic |
| Unit cell dimensions | a = 15.1326 (17) Å |
| | b = 6.9630 (8) Å |
| | c = 19.229 (2) Å |
| | α = 90° |
| | β = 108.087 (2)° |
| | γ = 90° |
| Z (per formula) | 4 |
| Density (g/cm³) | 1.360 |
| R | 0.0471 |

4. The crystalline form of the compound 3-isopropyl-6-[4-(2,5-difluoro-phenyl)-oxazol-5-yl]-[1,2,4]triazolo[4,3-a]pyridine having powder x-ray diffraction peaks at angle 2-theta of 9.1, 13.8, 17.4 and 22.6 degrees.

5. The crystalline form of the compound 3-isopropyl-6-[4-(2,5-difluoro-phenyl)-oxazol-5-yl]-[1,2,4]triazolo[4,3-a]pyridine having powder x-ray diffraction peaks at angle 2-theta of 8.5, 11.2, 14.8, 16.9, 17.1, 19.7, 22.3, 26.0 and 27.9 degrees.

6. The crystalline form of the compound 3-isopropyl-6-[4-(2,5-difluoro-phenyl)-oxazol-5-yl]-[1,2,4]triazolo[4,3-a]

pyridine having powder x-ray diffraction peaks at angle 2-theta of 7.4, 12.8, 14.8, 19.6, 22.3, 25.7 and 26.8 degrees.

7. The crystalline form of the compound 3-isopropyl-6-[4-(2,5-difluoro-phenyl)-oxazol-5-yl]-[1,2,4]triazolo[4,3-a]pyridine having powder x-ray diffraction peaks at angle 2-theta of 6.6, 13.8, 16.0, 17.3, 17.6, 22.5, 25.6 and 26.4 degrees.

8. The crystalline form of the compound 3-isopropyl-6-[4-(2,5-difluoro-phenyl)-oxazol-5-yl]-[1,2,4]triazolo[4,3-a]pyridine having powder x-ray diffraction peaks at angle 2-theta of 7.7, 8.4, 15.5, 17.2, 23.0, 26.7 and 28.6 degrees.

9. The crystalline form of the compound 3-isopropyl-6-[4-(2,5-difluoro-phenyl)-oxazol-5-yl]-[1,2,4]triazolo[4,3-a]pyridine having a $^{13}$C ss-NMR chemical shifts of 159.2, 157.2, 156.0, 154.9, 153.0, 150.2, 144.4, 142.4, 129.2, 125.3, 123.7, 121.9, 112.0, 118.3, 116.4, 114.9, 24.8, 20.8, 18.7, and 17.0 ppm.

10. The crystalline form of the compound 3-isopropyl-6-[4-(2,5-difluoro-phenyl)-oxazol-5-yl]-[1,2,4]triazolo[4,3-a]pyridine, having a $^{13}$C ss-NMR chemical shifts of 159.2, 157.2, 156.0, 154.9, 153.0, 150.2, 144.4, 142.4, 129.2, 125.3, 123.7, 121.9, 112.0, 118.3, 116.4, 114.9, 24.8, 20.8, 18.7, and 17.0 ppm and having a melting endotherm at 172–175° C.

11. The crystalline form of the compound 3-isopropyl-6-[4-(2,5-difluoro-phenyl)-oxazol-5-yl]-[1,2,4]triazolo[4,3-a]pyridine according to claim 5, having a $^{13}$C ss-NMR chemical shifts of 159.2, 157.2, 156.0, 154.9, 153.0, 150.2, 144.4, 142.4, 129.2, 125.3, 123.7, 121.9, 112.0, 118.3, 116.4, 114.9, 24.8, 20.8, 18.7, and 17.0 and a melting endotherm at 173–175° C.

12. The crystalline form of the compound 3-isopropyl-6-[4-(2,5-difluoro-phenyl)-oxazol-5-yl]-[1,2,4]triazolo[4,3-a]pyridine according to claim 2, having a $^{13}$C ss-NMR chemical shifts of 159.2, 157.2, 156.0, 154.9, 153.0, 150.2, 144.4, 142.4, 129.2, 125.3, 123.7, 121.9, 112.0, 118.3, 116.4, 114.9, 24.8, 20.8, 18.7, and 17.0 and a Differential Scanning Calorimetry melting endotherm at 173–175° C. and powder x-ray diffraction peaks at angle 2-theta of 8.5, 11.2, 14.8, 16.9, 19.7, 22.3, 26.0 and 27.9 degrees.

13. The crystalline form of the compound 3-isopropyl-6-[4-(2,5-difluoro-phenyl)-oxazol-5-yl]-[1,2,4]triazolo[4,3-a]pyridine according to claim 4, having thermal events between 105–125° C., 148° C. and 173° C.

14. The crystalline form of the compound 3-isopropyl-6-[4-(2,5-difluoro-phenyl)-oxazol-5-yl]-[1,2,4]triazolo[4,3-a]pyridine according to claim 1, having powder x-ray defraction peaks at angle 2-theta of 9.1, 13.8, 17.4 and 22.6 and thermal events between 105–125° C., 148° C. and 173° C.

15. The crystalline form of the compound 3-isopropyl-6-[4-(2,5-difluoro-phenyl)-oxazol-5-yl]-[1,2,4]triazolo[4,3-a]pyridine according to claim 7, having a broad endothermic event between 30–120° C. and a melting endotherm at 172–175° C.

16. The crystalline form of the compound 3-isopropyl-6-[4-(2,5-difluoro-phenyl)-oxazol-5-yl]-[1,2,4]triazolo[4,3-a]pyridine according to claim 3, having powder x-ray defraction peaks at angle 2-theta of 6.6, 13.8, 16.0, 17.3, 17.6, 22.5, 25.6 and 26.4 and a broad endothermic event between 30–120° C. and a melting endotherm at 177° C.

17. The crystalline form of the compound 3-isopropyl-6-[4-(2,5-difluoro-phenyl)-oxazol-5-yl]-[1,2,4]triazolo[4,3-a]pyridine according to claim 8, having an endotherm/exothermic event at between 70–120° C. and a melting endotherm at 175–177° C.

* * * * *